(12) United States Patent
Nishida

(10) Patent No.: US 12,274,999 B2
(45) Date of Patent: *Apr. 15, 2025

(54) WATER ABSORBENT RESIN PARTICLES, ABSORBENT, ABSORBENT ARTICLE AND LIQUID SUCTION POWER MEASUREMENT METHOD

(71) Applicant: SUMITOMO SEIKA CHEMICALS CO., LTD., Hyogo (JP)

(72) Inventor: Moe Nishida, Himeji (JP)

(73) Assignee: SUMITOMO SEIKA CHEMICALS CO., LTD., Hyogo (JP)

( * ) Notice: Subject to any disclaimer, the term of this patent is extended or adjusted under 35 U.S.C. 154(b) by 707 days.

This patent is subject to a terminal disclaimer.

(21) Appl. No.: 17/299,688

(22) PCT Filed: Dec. 12, 2019

(86) PCT No.: PCT/JP2019/048823
§ 371 (c)(1),
(2) Date: Jun. 3, 2021

(87) PCT Pub. No.: WO2020/122219
PCT Pub. Date: Jun. 18, 2020

(65) Prior Publication Data
US 2022/0055014 A1    Feb. 24, 2022

(30) Foreign Application Priority Data

Dec. 12, 2018 (JP) .................................. 2018-232724
Dec. 12, 2018 (JP) .................................. 2018-232726
(Continued)

(51) Int. Cl.
*B01J 20/26* (2006.01)
*A61F 13/53* (2006.01)
(Continued)

(52) U.S. Cl.
CPC ............. *B01J 20/267* (2013.01); *A61F 13/53* (2013.01); *B01J 20/103* (2013.01); *B01J 20/24* (2013.01);
(Continued)

(58) Field of Classification Search
CPC ........ B01J 20/267; B01J 20/103; B01J 20/24; B01J 20/28016; B01J 20/2805;
(Continued)

(56) References Cited

U.S. PATENT DOCUMENTS

2008/0280154 A1* 11/2008 Kobushi ................. A61L 15/60
524/558

FOREIGN PATENT DOCUMENTS

CN       102648218      8/2012
EP       1609810       12/2005
(Continued)

OTHER PUBLICATIONS

English Translation of JP2018039944A (Year: 2018).*
(Continued)

*Primary Examiner* — Andrew J. Oyer
(74) *Attorney, Agent, or Firm* — HSML P.C.

(57) ABSTRACT

Disclosed is water-absorbent resin particles, in which a value of non-pressurization DW after 3 minutes is 14 ml/g or more, and a value of liquid suction power after 3 minutes measured by the following method is 11 ml/g or more. A liquid suction power measurement method: 0.3 g of the water-absorbent resin particles is uniformly dispersed in a cylindrical container having a mesh-like bottom and having an inner diameter of 26 mm; the cylindrical container is placed in a container containing 40 g of a physiological saline solution, the water-absorbent resin particles are caused to absorb the physiological saline solution for 30 minutes from the bottom of the cylindrical container, and
(Continued)

thereby a swollen gel is obtained; and non-pressurization DW, which is measured in a state where another 0.3 g of the water-absorbent resin particles is uniformly dispersed on the swollen gel in the cylindrical container, is defined as liquid suction power.

5 Claims, 4 Drawing Sheets

(30) Foreign Application Priority Data

| Dec. 12, 2018 | (JP) | ................................ 2018-232728 |
|---|---|---|
| Dec. 12, 2018 | (JP) | ................................ 2018-232843 |
| Dec. 12, 2018 | (JP) | ................................ 2018-232847 |
| Dec. 12, 2018 | (JP) | ................................ 2018-232848 |
| Dec. 12, 2018 | (JP) | ................................ 2018-232850 |
| Dec. 12, 2018 | (JP) | ................................ 2018-232851 |
| Dec. 12, 2018 | (JP) | ................................ 2018-232856 |
| Dec. 12, 2018 | (JP) | ................................ 2018-232857 |
| Jan. 30, 2019 | (JP) | ................................ 2019-014531 |
| Mar. 22, 2019 | (JP) | ................................ 2019-055302 |

(51) Int. Cl.

| *A61F 13/84* | (2006.01) |
|---|---|
| *B01J 20/10* | (2006.01) |
| *B01J 20/24* | (2006.01) |
| *B01J 20/28* | (2006.01) |
| *G01N 13/04* | (2006.01) |

(52) U.S. Cl.
CPC ...... *B01J 20/28016* (2013.01); *B01J 20/2805* (2013.01); *G01N 13/04* (2013.01); *A61F 2013/530744* (2013.01); *A61F 2013/8491* (2013.01)

(58) Field of Classification Search
CPC ........ B01J 2220/46; B01J 20/26; B01J 20/28; A61F 13/53; A61F 2013/530744; A61F 2013/8491; A61F 2013/530671; A61F 2013/530737; A61F 2013/530481; G01N 13/04; C08J 2333/02; C08J 3/075; C08J 3/12; C08J 3/24; C08F 2/32
See application file for complete search history.

(56) References Cited

FOREIGN PATENT DOCUMENTS

| EP | 1623998 | 2/2006 |
|---|---|---|
| EP | 1714985 | 10/2006 |
| EP | 1900755 | 3/2008 |
| EP | 2893974 | 7/2015 |
| JP | H9-124879 | 5/1997 |
| JP | H9-323038 | 12/1997 |
| JP | 2003-088551 | 3/2003 |
| JP | 2003-088552 | 3/2003 |
| JP | 2006-176570 | 7/2006 |
| JP | 2009-019065 | 1/2009 |
| JP | 2010-116548 | 5/2010 |
| JP | 2016-120083 | 7/2016 |
| JP | 2016-121297 | 7/2016 |
| JP | 2018-039944 | 3/2018 |
| JP | 2018039944 A * | 3/2018 |
| JP | 6351505 | 7/2018 |
| KR | 10-2008-0039398 | 5/2008 |
| WO | 96/005234 | 2/1996 |
| WO | 2004/101628 | 11/2004 |
| WO | 2005/063825 | 7/2005 |
| WO | 2007/000452 | 1/2007 |
| WO | 2014/038324 | 3/2014 |
| WO | 2016/104374 | 6/2016 |
| WO | 2017/170605 | 10/2017 |
| WO | 2018/181277 | 10/2018 |
| WO | 2018/181565 | 10/2018 |

OTHER PUBLICATIONS

International Preliminary Report on Patentability of PCT/JP2019/048823, Jun. 24, 2021, 12 pages.
International Search Report of PCT/JP2019/048823, Mar. 17, 2020, 4 pages.
"Certificate of Experimental Results", Apr. 6, 2022, 6 pages; English translation provided.
"Database WPI, Week 201821", Thomson Scientific, London, GB; AN 2018-212073, Mar. 15, 2018, XP002807428, 2 pages.
"Database WPI, Week 201646", Thomson Scientific, London, GB; AN 2016-40488B, Jul. 7, 2016, XP002807429, 3 pages.
"Database WPI, Week 199729", Thomson Scientific, London, GB; AN 1997-316703, May 13, 1997, XP002807430, 2 pages.
The partial supplementary European search report of European Patent Application No. 19895638.5, Sep. 12, 2022, 15 pages.

* cited by examiner

WATER ABSORBENT RESIN PARTICLES, ABSORBENT, ABSORBENT ARTICLE AND LIQUID SUCTION POWER MEASUREMENT METHOD

TECHNICAL FIELD

The present invention relates to water-absorbent resin particles, an absorbent, an absorbent article, and a method for measuring liquid suction power.

BACKGROUND ART

A water-absorbent resin is used in the field of sanitary products and the like, and specifically, it is used as a material for an absorbent contained in an absorbent article such as a diaper (for example, Patent Literature 1).

CITATION LIST

Patent Literature

[Patent Literature 1] JP 6351505

SUMMARY OF INVENTION

Technical Problem

Absorbent articles such as diapers has an absorbent that absorbs and retains body fluids such as urine and menstrual blood. The absorbent generally contains water-absorbent resin particles and fibrous materials such as pulp, where the fibrous materials are entwined with each other, or the fibrous materials and the water-absorbent resin particles are entwined with each other. In recent years, absorbent articles in which a proportion of fibrous materials in an absorbent is low have tended to be preferred. In a case where the proportion of the fibrous materials in the absorbent is low, and when a shearing force is applied to the absorbent after it absorbs a liquid due to, for example, a load of body weight and the like while an absorbent article is worn, deformation of the absorbent such as tearing of the absorbent from its inside may occur. The absorbent in which tearing has been occurred cannot sufficiently exhibit its absorption performance.

An object of the present invention is to provide water-absorbent resin particles capable of inhibiting occurrence of tearing in an absorbent after absorption.

Solution to Problem

Water-absorbent resin particles of the present invention have a value of non-pressurization DW after 3 minutes of 14 ml/g or more, and a value of liquid suction power after 3 minutes measured by the following method of 11 ml/g or more.

A liquid suction power measurement method: 0.3 g of the water-absorbent resin particles is uniformly dispersed in a cylindrical container having a mesh-like bottom and having an inner diameter of 26 mm; the cylindrical container is placed in a container containing 40 g of a physiological saline solution, the water-absorbent resin particles are caused to absorb the physiological saline solution for 30 minutes from the bottom of the cylindrical container, and thereby a swollen gel is obtained; and non-pressurization DW, which is measured in a state where another 0.3 g of the water-absorbent resin particles is uniformly dispersed on the swollen gel in the cylindrical container, is defined as liquid suction power.

In the water-absorbent resin particles, a content of silica particles is preferably 1.8% by mass or less.

The present invention further provides an absorbent containing the water-absorbent resin particles.

The present invention still further provides an absorbent article including the absorbent.

The absorbent article may be a diaper.

A method for measuring liquid suction power of the present invention includes: causing water-absorbent resin particles to absorb a test solution to obtain a swollen gel; placing water-absorbent resin particles, which are of the same type as the water-absorbent resin particles, on a gel layer formed from the swollen gel to obtain a test sample containing the gel layer and the water-absorbent resin particles; and measuring non-pressurization DW with the test sample as an evaluation target.

The present invention still further provides a method for producing water-absorbent resin particles, the method including evaluating liquid suction power of the water-absorbent resin particles by the above method for measuring liquid suction power.

Advantageous Effects of Invention

According to the present invention, water-absorbent resin particles capable of inhibiting occurrence of tearing in an absorbent after absorption are provided.

DESCRIPTION OF EMBODIMENTS

Figure 1:
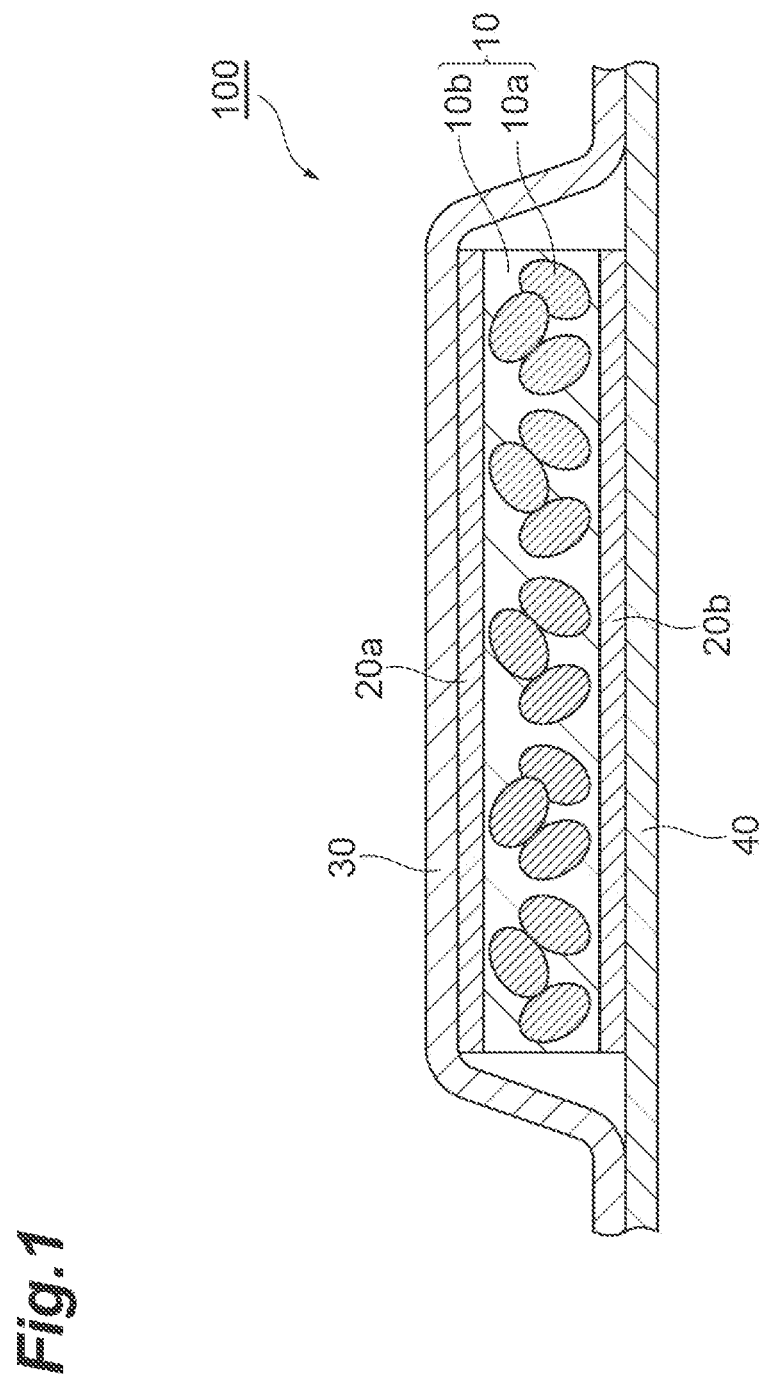
FIG. 1 is a cross-sectional view showing an example of an absorbent article.

Hereinafter, suitable embodiments of the present invention will be described in detail. However, the present invention is not limited to the following embodiments.

In the present specification, "acrylic" and "methacrylic" are collectively referred to as "(meth)acrylic." "Acrylate" and "methacrylate" are also referred to as "(meth)acrylate." Regarding numerical value ranges described in a stepwise manner in the present specification, an upper limit value or a lower limit value of a numerical value range in a certain step can be arbitrarily combined with an upper limit value or a lower limit value of a numerical value range in another step. In a numerical value range described in the present specification, an upper limit value or a lower limit value of the numerical value range may be replaced with a value shown in examples. The term "water-soluble" means that a solubility of 5% by mass or more is exhibited in water at 25° C. For materials exemplified in the present specification, one kind may be used alone, or two or more kinds may be used in combination. In a case where there are a plurality of substances corresponding to each of the components in a composition, a content of each of the components in the composition means a total amount of the plurality of substances present in the composition unless otherwise specified.

Water-absorbent resin particles according to the present embodiment have a value of non-pressurization DW after 3 minutes of 14 ml/g or more, and a value of liquid suction power after 3 minutes measured by a method to be described later of 11 ml/g or more.

The non-pressurization Demand Wettability (DW) is an index indicating a suction performance represented by an amount of a physiological saline solution (an aqueous solution of NaCl at a concentration of 0.9% by mass, the same applies hereinafter) which is absorbed by the water-absorbent resin particles under no pressurization until the elapse of a predetermined time after the water-absorbent resin particles are brought into contact with the physiological saline solution. The non-pressurization DW is represented by an amount of absorption (ml) per 1 g of the water-absorbent resin particles before absorbing a physiological saline solution. The value of non-pressurization DW after 3 minutes means an amount of absorption 3 minutes after the water-absorbent resin particles are brought into contact with a physiological saline solution. A target for which non-pressurization DW is measured is a dried product of the water-absorbent resin particles.

A value of non-pressurization DW after 3 minutes may be 20 ml/g or more, 25 ml/g or more, or 30 ml/g or more. A value of non-pressurization DW after 3 minutes may be, for example, 55 ml/g or less, 50 ml/g or less, 45 ml/g or less, 40 ml/g or less, or 35 ml/g or less. A value of non-pressurization DW after 3 minutes of the water-absorbent resin particles may be 14 to 55 ml/g, 14 to 50 ml/g, 14 to 45 ml/g, 14 to 40 ml/g, or 20 to 40 ml/g. The value of non-pressurization DW after 3 minutes is a value measured by a method described in Examples to be described later.

The liquid suction power of the water-absorbent resin particles is a value measured by a measurement method newly discovered by the inventors of the present invention. A method for measuring liquid suction power is based on a non-pressurization DW measurement method, and is characterized in that a dried product of the water-absorbent resin particles, and a swollen gel obtained after water absorption are used in combination for measurement targets. In the non-pressurization DW measurement method, a test solution is directly absorbed by a dried product of the water-absorbent resin particles, whereas in the measurement of the liquid suction power, a layer of a swollen gel (gel layer) is present between a dried product of the water-absorbent resin particles and a test solution, where the layer is formed after the test solution is absorbed by water-absorbent resin particles of the same type.

The liquid suction power is specifically measured by the following method. 0.3 g of the water-absorbent resin particles is uniformly dispersed in a cylindrical container having a mesh-like bottom and having an inner diameter of 26 mm. The cylindrical container is placed in a container containing 40 g of a physiological saline solution that is a test solution, the water-absorbent resin particles are caused to absorb the physiological saline solution for 30 minutes from the bottom of the cylindrical container, and thereby a swollen gel is obtained. Another 0.3 g of the water-absorbent resin particles (dried product) is uniformly dispersed on the swollen gel in the cylindrical container. An amount of absorption (ml) of the physiological saline solution per 1 g of the water-absorbent resin particles (dried product) is defined as liquid suction power, where the amount is measured with the swollen gel and the dried product of the water-absorbent resin particles on the swollen gel as measurement targets, and measured in the same manner as in the non-pressurization DW measurement method. The value of liquid suction power after 3 minutes means an amount of absorption 3 minutes after the physiological saline solution, which has permeated the swollen gel, comes into contact with the dried product of the water-absorbent resin particles on the swollen gel.

A value of liquid suction power after 3 minutes of the water-absorbent resin particles may be 12 ml/g or more, 13 ml/g or more, 15 ml/g or more, or 17 ml/g or more. A value of liquid suction power after 3 minutes of the water-absorbent resin particles may be, for example, 25 ml/g or less, 23 ml/g or less, or 20 ml/g or less. A value of liquid suction power after 3 minutes of the water-absorbent resin particles may be 11 to 25 ml/g, 12 to 25 ml/g, 13 to 25 ml/g, 15 to 25 ml/g, or 15 to 23 ml/g. A case in which a value of liquid suction power after 3 minutes is within the above range is preferable, because then occurrence of tearing of the absorbent is likely to be further inhibited.

The water-absorbent resin particles according to the present embodiment can have a high water absorption capacity with respect to a physiological saline solution. A water retention capacity of the water-absorbent resin particles for a physiological saline solution may be 30 g/g or more, 32 g/g or more, 35 g/g or more, 37 g/g or more, 39 g/g or more, or 40 g/g or more. A water retention capacity of the water-absorbent resin particles for a physiological saline solution may be 60 g/g or less, 55 g/g or less, 50 g/g or less, 48 g/g or less, or 45 g/g or less. A water retention capacity of the water-absorbent resin particles for a physiological saline solution may be 30 to 60 g/g, 30 to 55 g/g, 30 to 50 g/g, 30 to 45 g/g, 32 to 45 g/g, 35 to 45 g/g, 35 to 42 g/g, or 32 to 42 g/g. The water retention capacity for a physiological saline solution is measured by a method described in Examples to be described later.

Examples of shapes of the water-absorbent resin particles include a substantially spherical shape, a crushed shape, and a granular shape. A median particle size of the water-absorbent resin particles may be 250 to 850 µm, 300 to 700 µm, or 300 to 600 µm. The water-absorbent resin particles according to the present embodiment may have a desired particle size distribution at a timing at which polymer particles are obtained by a production method to be described later, but their particle size distribution may be adjusted by performing operations such as adjustment of a particle size through classification with a sieve.

The water-absorbent resin particles according to the present embodiment can contain, for example, a crosslinked polymer formed by polymerization of monomers including ethylenically unsaturated monomers. The crosslinked polymer has a monomer unit derived from an ethylenically unsaturated monomer. That is, the water-absorbent resin particles according to the present embodiment can have a structural unit derived from ethylenically unsaturated monomers.

Examples of methods for polymerizing the monomers include a reverse-phase suspension polymerization method, an aqueous solution polymerization method, a bulk polymerization method, and a precipitation polymerization method. Among them, the reverse-phase suspension polymerization method or the aqueous solution polymerization method is preferable from the viewpoints of facilitating securement of favorable water absorption characteristics of the obtained water-absorbent resin particles and control of a polymerization reaction. Hereinbelow, a method for polymerizing ethylenically unsaturated monomers will be described with the reverse-phase suspension polymerization method as an example.

An ethylenically unsaturated monomer is preferably water-soluble. Examples thereof include (meth)acrylic acid and a salt thereof, 2-(meth)acrylamide-2-methylpropane-sulfonic acid and a salt thereof, (meth)acrylamide, N,N-dimethyl (meth)acrylamide, 2-hydroxyethyl (meth)acrylate, N-methylol (meth)acrylamide, polyethylene glycol mono (meth)acrylate, N,N-diethylaminoethyl (meth)acrylate, N,N-diethylaminopropyl (meth)acrylate, and diethylaminopropyl (meth)acrylamide. In a case where an ethylenically unsaturated monomer has an amino group, the amino group may be quaternarized. A functional group such as a carboxyl group and an amino group, which is contained in the monomer, can function as a crosslinkable functional group in a surface crosslinking process to be described later. These ethylenically unsaturated monomers may be used alone or in a combination of two or more kinds thereof.

Among them, from the viewpoint of high industrial availability, the ethylenically unsaturated monomer preferably includes at least one compound selected from the group consisting of (meth)acrylic acid and a salt thereof, acrylamide, methacrylamide, and N,N-dimethyl acrylamide, and more preferably includes at least one compound selected from the group consisting of (meth)acrylic acid and a salt thereof, and acrylamide. The ethylenically unsaturated monomer more preferably includes at least one compound selected from the group consisting of (meth)acrylic acid and a salt thereof from the viewpoint of further enhancing water absorption characteristics.

For the monomer, a monomer other than the above-mentioned ethylenically unsaturated monomers may be partially used. Such a monomer can be used by, for example, being mixed with an aqueous solution containing the ethylenically unsaturated monomers. It is preferable that a usage amount of the ethylenically unsaturated monomers be 70 to 100 mol % with respect to a total amount of the monomers. Among the examples, it is more preferable that an amount of (meth)acrylic acid and a salt thereof be 70 to 100 mol % with respect to the total amount of the monomers.

Usually, the ethylenically unsaturated monomers are suitably used in a form of an aqueous solution. In general, it is sufficient for a concentration of the ethylenically unsaturated monomers in an aqueous solution containing the ethylenically unsaturated monomers (hereinafter, referred to as an aqueous solution of monomers) to be 20% by mass or more and a saturated concentration or less, and it is preferably 25% to 70% by mass, and is more preferably 30% to 55% by mass. Examples of water to be used include tap water, distilled water, and ion exchange water.

In a case where ethylenically unsaturated monomers to be used have an acidic group, an aqueous solution of monomers may be used after neutralizing this acidic group with an alkaline neutralizing agent. From the viewpoint of increasing an osmotic pressure of the obtained water-absorbent resin particles and thereby further enhancing water absorption characteristics such as a water retention capacity, a degree of neutralization in the ethylenically unsaturated monomers by the alkaline neutralizing agent is 10 to 100 mol %, is preferably 50 to 90 mol %, and is more preferably 60 to 80 mol % of the acidic group in the ethylenically unsaturated monomers. Examples of alkaline neutralizing agents include alkali metal salts such as sodium hydroxide, sodium carbonate, sodium hydrogen carbonate, potassium hydroxide, and potassium carbonate; and ammonia. These alkaline neutralizing agents may be used in a form of an aqueous solution to simplify a neutralizing operation. The above-mentioned alkaline neutralizing agents may be used alone or in combination of two or more kinds thereof.

Neutralization of the acidic groups in the ethylenically unsaturated monomers can be performed by, for example, adding an aqueous solution of sodium hydroxide, potassium hydroxide, or the like dropwise to the aqueous solution of monomers and mixing them.

In the reverse-phase suspension polymerization method, an aqueous solution of monomers is dispersed in a hydrocarbon dispersion medium in the presence of a surfactant, and polymerization of ethylenically unsaturated monomers is performed using a radical polymerization initiator or the like.

Examples of surfactants include nonionic surfactants and anionic surfactants. Examples of nonionic surfactants include sorbitan fatty acid esters, (poly)glycerin fatty acid esters (where "(poly)" means both of a case with the prefix "poly" and a case without the prefix "poly," and the same applies hereinbelow), sucrose fatty acid esters, polyoxyethylene sorbitan fatty acid esters, polyoxyethylene glycerin fatty acid esters, sorbitol fatty acid esters, polyoxyethylene sorbitol fatty acid esters, polyoxyethylene alkyl ethers, polyoxyethylene alkylphenyl ethers, polyoxyethylene castor oil, polyoxyethylene hydrogenated castor oil, alkylallyl formaldehyde condensed polyoxyethylene ethers, polyoxyethylene polyoxypropylene block copolymers, polyoxyethylene polyoxypropyl alkyl ethers, and polyethylene glycol fatty acid esters. Examples of anionic surfactants include fatty acid salts, alkylbenzene sulfonate, alkylmethyl taurate, polyoxyethylene alkylphenyl ether sulfuric acid ester salts, polyoxyethylene alkyl ether sulfonic acid salts, phosphoric acid esters of polyoxyethylene alkyl ethers, and phosphoric acid esters of polyoxyethylene alkyl allyl ethers. Among them, the surfactant preferably includes at least one compound selected from the group consisting of sorbitan fatty acid esters, polyglycerin fatty acid esters, and sucrose fatty acid esters, from the viewpoints that then, a state of a W/O type reverse-phase suspension becomes favorable, water-absorbent resin particles are likely to be obtained with suitable particle sizes, and industrial availability becomes high. Furthermore, the surfactant more preferably includes sucrose fatty acid esters from the viewpoint that water absorption characteristics of the obtained water-absorbent resin particles are then improved. These surfactants may be used alone or in combination of two or more kinds thereof.

An amount of the surfactant is preferably 0.05 to 10 parts by mass, is more preferably 0.08 to 5 parts by mass, and is even more preferably 0.1 to 3 parts by mass, with respect to 100 parts by mass of the aqueous solution of the ethylenically unsaturated monomers, from the viewpoint that a sufficient effect is obtained within these usage amounts, and these amounts are economic.

Furthermore, a polymeric dispersant may be used in combination with the above-mentioned surfactant. Examples of polymeric dispersants include maleic anhydride-modified polyethylene, maleic anhydride-modified polypropylene, a maleic anhydride-modified ethylene-propylene copolymer, a maleic anhydride-modified EPDM (ethylene propylene diene terpolymer), maleic anhydride-modified polybutadiene, a maleic anhydride-ethylene copolymer, a maleic anhydride-propylene copolymer, a maleic anhydride-ethylene-propylene copolymer, a maleic anhydride-butadiene copolymer, polyethylene, polypropylene, an ethylene-propylene copolymer, oxidized polyethylene, oxidized polypropylene, an oxidized ethylene-propylene copolymer, an ethylene-acrylic acid copolymer, ethyl cellulose, ethyl hydroxyethyl cellulose, and the like. Among these polymeric dispersants, particularly from the viewpoint of dispersion stability of monomers, it is preferable to use maleic anhydride-modified polyethylene, maleic anhydride-modified polypropylene, a maleic anhydride-modified ethylene-propylene copolymer, a maleic anhydride-ethylene copolymer, a maleic anhydride-propylene copolymer, a maleic anhydride-ethylene-propylene copolymer, polyethylene, polypropylene, an ethylene-propylene copolymer, oxidized polyethylene, oxidized polypropylene, and an oxidized ethylene-propylene copolymer. These polymeric dispersants may be used alone or in combination of two or more kinds thereof.

An amount of the polymeric dispersant is preferably 0.05 to 10 parts by mass, is more preferably 0.08 to 5 parts by mass, and is even more preferably 0.1 to 3 parts by mass, with respect to 100 parts by mass of the aqueous solution of the ethylenically unsaturated monomers, from the viewpoint that a sufficient effect is obtained within these usage amounts, and these amounts are economic.

A radical polymerization initiator is preferably water-soluble. Examples thereof include persulfates such as potassium persulfate, ammonium persulfate, and sodium persulfate; peroxides such as methyl ethyl ketone peroxide, methyl isobutyl ketone peroxide, di-t-butyl peroxide, t-butyl cumyl peroxide, t-butyl peroxyacetate, t-butyl peroxyisobutyrate, t-butyl peroxypivalate, and hydrogen peroxide; and azo compounds such as 2,2'-azobis(2-amidinopropane) dihydrochloride, 2,2'-azobis[2-(N-phenylamidino)propane]dihydrochloride, 2,2'-azobis[2-(N-allylamidino)propane]dihydrochloride, 2,2'-azobis[2-(2-imidazolin-2-yl)propane] dihydrochloride, 2,2'-azobis{2-[1-(2-hydroxyethyl)-2-imidazolin-2-yl]propane}dihydrochloride, 2,2'-azobis{2-methyl-N-[1,1-bis(hydroxymethyl)-2-hydroxyethyl] propionamide}, 2,2'-azobis[2-methyl-N-(2-hydroxyethyl)-propionamide], and 4,4'-azobis(4-cyanovaleric acid). Among them, potassium persulfate, ammonium persulfate, sodium persulfate, 2,2'-azobis(2-amidinopropane) dihydrochloride, 2,2'-azobis[2-(2-imidazolin-2-yl)propane]dihydrochloride, and 2,2'-azobis {2-[I-(2-hydroxyethyl)-2-imidazolin-2-yl]propane}dihydrochloride are preferred. These radical polymerization initiators may be used alone or in combination of two or more kinds thereof.

A usage amount of the radical polymerization initiator may be 0.00005 to 0.01 moles with respect to 1 mole of the ethylenically unsaturated monomers. A case in which a usage amount of the radical polymerization initiator is 0.00005 moles or more is efficient, because then a polymerization reaction is not required to be performed for a long period of time. In a case where a usage amount thereof is 0.01 moles or less, a rapid polymerization reaction is unlikely to occur.

The radical polymerization initiator can also be used as a redox polymerization initiator when it is used in combination with a reducing agent such as sodium sulfite, sodium hydrogen sulfite, ferrous sulfate, and L-ascorbic acid.

In a polymerization reaction, a chain transfer agent may be contained in an aqueous solution of the ethylenically unsaturated monomers used for the polymerization. Examples of chain transfer agents include hypophosphites, thiols, thiolic acids, secondary alcohols, and amines.

Furthermore, a thickener may be contained in the aqueous solution of the ethylenically unsaturated monomers used for the polymerization to control a particle size of the water-absorbent resin particles. As the thickener, it is possible to use, for example, hydroxyethyl cellulose, hydroxypropyl cellulose, methyl cellulose, carboxymethyl cellulose, polyethylene glycol, polyacrylamide, polyethyleneimine, dextrin, sodium alginate, polyvinyl alcohol, polyvinylpyrrolidone, polyethylene oxide, and the like. In a case where stirring speeds in the polymerization are the same, a median particle size of particles to be obtained is likely to become large as a viscosity of the aqueous solution of the ethylenically unsaturated monomers becomes high.

The hydrocarbon dispersion medium may include at least one compound selected from the group consisting of a chained aliphatic hydrocarbon having 6 to 8 carbon atoms and an alicyclic hydrocarbon having 6 to 8 carbon atoms. Examples of hydrocarbon dispersion media include chained aliphatic hydrocarbons such as n-hexane, n-heptane, 2-methylhexane, 3-methylhexane, 2,3-dimethylpentane, 3-ethylpentane, and n-octane; alicyclic hydrocarbons such as cyclohexane, methylcyclohexane, cyclopentane, methylcyclopentane, trans-1,2-dimethylcyclopentane, cis-1,3-dimethylcyclopentane, and trans-1,3-dimethylcyclopentane; and aromatic hydrocarbons such as benzene, toluene, and xylene. These hydrocarbon dispersion media may be used alone or in combination of two or more kinds thereof. For the hydrocarbon dispersion medium, n-heptane, cyclohexane, or both n-heptane and cyclohexane may be contained, from the viewpoints of high industrial availability and stable qualities. Furthermore, from the same viewpoints, as a mixture of the hydrocarbon dispersion media, for example, a commercially available Exxsol Heptane (manufactured by ExxonMobil Chemical: containing n-heptane and 75% to 85% of hydrocarbons of isomers thereof) may be used.

A usage amount of the hydrocarbon dispersion medium is preferably 30 to 1,000 parts by mass, is more preferably 40 to 500 parts by mass, and is even more preferably 50 to 300 parts by mass, with respect to 100 parts by mass of the aqueous solution of monomers, from the viewpoint that polymerization heat is then appropriately removed, and thereby a polymerization temperature is easily controlled. In a case where a usage amount of the hydrocarbon dispersion medium is 30 parts by mass or more, there is a tendency that it becomes easy to control a polymerization temperature. In a case where a usage amount of the hydrocarbon dispersion medium is 1,000 parts by mass or less, there is a tendency that productivity of polymerization is improved, which is economic.

In general, internal crosslinking may occur by self-crosslinking upon the polymerization, but internal crosslinking may be carried out by further using an internal crosslinking agent, and thereby water absorption characteristics of the water-absorbent resin particles may be controlled. Examples of internal crosslinking agents to be used include di- or tri(meth)acrylic acid esters of polyols such as ethylene glycol, propylene glycol, trimethylolpropane, glycerin, polyoxyethylene glycol, polyoxypropylene glycol, and polyglycerin; unsaturated polyesters obtained by reacting the above mentioned polyols with unsaturated acids such as maleic acid and fumaric acid; bis(meth)acrylamides such as N,N'-methylenebis(meth)acrylamide; di- or tri(meth)acrylic acid esters obtained by reacting a polyepoxide with (meth) acrylic acid; carbamyl di(meth)acrylate esters obtained by reacting a polyisocyanate such as tolylene diisocyanate and hexamethylene diisocyanate with hydroxyethyl (meth)acrylate; compounds having two or more polymerizable unsaturated groups, such as allylated starch, allylated cellulose, diallyl phthalate, N,N',N"-triallylisocyanurate, and divinylbenzene; polyglycidyl compounds such as (poly)ethylene glycol diglycidyl ether, (poly)propylene glycol diglycidyl ether, (poly)glycerin diglycidyl ether, (poly)glycerin triglycidyl ether, (poly)propylene glycol polyglycidyl ether, and polyglycerol polyglycidyl ether; haloepoxy compounds such as epichlorohydrin, epibromohydrin, and α-methyl epichlorohydrin; and compounds having two or more reactive functional groups, such as isocyanate compounds including, for example, 2,4-tolylene diisocyanate and hexamethylene diisocyanate. Among these internal crosslinking agents, it is preferable to use a polyglycidyl compound, it is more preferable to use a diglycidyl ether compound, and it is particularly preferable to use (poly)ethylene glycol diglycidyl ether, (poly)propylene glycol diglycidyl ether, and (poly)glycerin diglycidyl ether. These crosslinking agents may be used alone or in combination of two or more kinds thereof.

An amount of the internal crosslinking agent is preferably 0 to 0.03 moles, is more preferably 0.00001 to 0.01 moles, and is even more preferably 0.00002 to 0.005 moles, per 1 mole of the ethylenically unsaturated monomer, from the viewpoints of inhibiting water-soluble properties by appropriately crosslinking the obtained polymer, and exhibiting a sufficient water absorption capacity.

An aqueous phase containing components such as an ethylenically unsaturated monomer, a radical polymerization initiator, and if necessary, an internal crosslinking agent; and an oil phase containing components such as a hydrocarbon dispersion medium, a surfactant, and if necessary, and a polymeric dispersant can be mixed and heated under stirring to carry out reverse-phase suspension polymerization in a water-in-oil system.

When performing the reverse-phase suspension polymerization, an aqueous solution of monomers which contains ethylenically unsaturated monomers is dispersed in a hydrocarbon dispersion medium in the presence of a surfactant and if necessary, a polymeric dispersant. In this case, a timing of adding the surfactant or the polymeric dispersant before the start of the polymerization reaction may be either before or after the addition of the aqueous solution of monomers.

Among them, it is preferable to carry out the polymerization after dispersing the aqueous solution of monomers in the hydrocarbon dispersion medium in which the polymeric dispersant has been dispersed, and then further dispersing the surfactant in the hydrocarbon dispersion medium, from the viewpoint that an amount of the hydrocarbon dispersion medium remaining in the obtained water-absorbent resin can then be easily reduced.

Such reverse-phase suspension polymerization can be carried out in one stage or in multiple stages of two or more stages. Furthermore, it is preferably carried out in two or three stages from the viewpoint of increasing productivity.

In a case where reverse-phase suspension polymerization is carried out in multiple stages of two or more stages, it is sufficient for stages after a second stage of reverse-phase suspension polymerization to be carried out in the same manner as in a first stage of reverse-phase suspension polymerization by adding ethylenically unsaturated monomers to a reaction mixture obtained in the first stage of polymerization reaction and mixing them, after performing the first stage of reverse-phase suspension polymerization. In reverse-phase suspension polymerization in each stage after the second stage, it is preferable to carry out reverse-phase suspension polymerization by adding, in addition to ethylenically unsaturated monomers, the above-mentioned radical polymerization initiator and internal crosslinking agent within a range of molar ratios of the respective components to the ethylenically unsaturated monomers, based on an amount of ethylenically unsaturated monomers added during reverse-phase suspension polymerization in each stage after the second stage. If necessary, the internal crosslinking agent may be used in reverse-phase suspension polymerization in each stage after the second stage. In a case where the internal crosslinking agent is used, it is preferable to carry out reverse-phase suspension polymerization by adding the internal crosslinking agent within a range of molar ratios of the respective components to the ethylenically unsaturated monomers based on an amount of ethylenically unsaturated monomers provided in each stage.

A temperature for the polymerization reaction varies depending on radical polymerization initiators used, and it is preferably 20° C. to 150° C., and is more preferably 40° C. to 120° C., from the viewpoint that the polymerization is then promptly performed, which shortens a polymerization time, and thereby economic efficiency increases, and that polymerization heat is then easily removed, and thereby the reaction is smoothly performed. A reaction time is generally 0.5 to 4 hours. Completion of the polymerization reaction can be confirmed from, for example, stop of temperature rising in the reaction system. Accordingly, a polymer of ethylenically unsaturated monomers is generally obtained in a state of a hydrous gel.

After the polymerization, post-polymerization crosslinking may be carried out by adding a crosslinking agent to the obtained hydrous gel polymer and heating them. By performing the post-polymerization crosslinking, a degree of crosslinking of the hydrous gel polymer can be increased, and thereby water absorption characteristics can be more preferably improved.

Examples of crosslinking agents for performing the post-polymerization crosslinking include polyols such as ethylene glycol, propylene glycol, 1,4-butanediol, trimethylolpropane, glycerin, polyoxyethylene glycol, polyoxypropylene glycol, and polyglycerin; compounds having two or more epoxy groups, such as (poly)ethylene glycol diglycidyl ether, (poly)propylene glycol diglycidyl ether, and (poly)glycerin diglycidyl ether; haloepoxy compounds such as epichlorohydrin, epibromohydrin, and α-methyl epichlorohydrin; compounds having two or more isocyanate groups such as 2,4-tolylene diisocyanate and hexamethylene diisocyanate; oxazoline compounds such as 1,2-ethylenebisoxazoline; carbonate compounds such as ethylene carbonate; and hydroxyalkylamide compounds such as bis[N,N-di(β-hydroxyethyl)]adipamide. Among them, polyglycidyl compounds such as (poly)ethylene glycol diglycidyl ether, (poly)glycerin diglycidyl ether, (poly) glycerin triglycidyl ether, (poly)propylene glycol polyglycidyl ether, and polyglycerol polyglycidyl ether are preferable. These crosslinking agents may be used alone or in combination of two or more kinds thereof.

An amount of the crosslinking agent used for the post-polymerization crosslinking is preferably 0 to 0.03 moles, is more preferably 0 to 0.01 moles, and is even more preferably 0.00001 to 0.005 moles, per 1 mole of the ethylenically unsaturated monomer, from the viewpoint of exhibiting suitable water absorption characteristics by appropriately crosslinking the obtained hydrous gel polymer.

It is sufficient for a timing for adding the post-polymerization crosslinking to be after polymerization of ethylenically unsaturated monomers used for the polymerization. In a case of multi-stage polymerization, the crosslinking agent is preferably added after the multi-stage polymerization. From the viewpoint of a water content (to be described later), it is preferable to add the crosslinking agent for the post-polymerization crosslinking within a region of [water content immediately after polymerization ±3% by mass], in consideration of heat generation during and after polymerization, retention due to process delay, system opening when a crosslinking agent is added, and fluctuation in moisture content due to addition of water associated with addition of a crosslinking agent.

Subsequently, drying is performed to remove water from the obtained hydrous gel polymer. By drying, polymer particles containing the polymer of ethylenically unsaturated monomers are obtained. Examples of drying methods include a method (a) in which the hydrous gel polymer in a state of being dispersed in a hydrocarbon dispersion medium is subjected to azeotropic distillation by heating from the outside, and the hydrocarbon dispersion medium is refluxed to remove water; a method (b) in which the hydrous gel polymer is taken out by decantation and dried under reduced pressure; and a method (c) in which the hydrous gel polymer is separated by filtration with a filter and dried under reduced pressure. Among them, the method (a) is preferably used for its simplicity in a production process.

Control over a particle size of the water-absorbent resin particle can be performed, for example, by adjusting a rotational speed of a stirrer during the polymerization reaction or by adding a powdery inorganic flocculating agent to the system after the polymerization reaction or at an initial time of drying. A particle size of the obtained water-absorbent resin particle can be increased by adding the flocculating agent. Examples of powdery inorganic flocculating agents include silica, zeolite, bentonite, aluminum oxide, talc, titanium dioxide, kaolin, clay, and hydrotalcite. Among them, silica, aluminum oxide, talc, or kaolin is preferable from the viewpoint of a flocculation effect.

In the reverse-phase suspension polymerization, the following method is preferable as a method of adding the powdery inorganic flocculating agent: a method in which a powdery inorganic flocculating agent is dispersed in a hydrocarbon dispersion medium of the same kind as that used in the polymerization, or water in advance, and then the mixture is mixed into a hydrocarbon dispersion medium containing a hydrous gel polymer under stirring.

In the production of the water-absorbent resin particles according to the present embodiment, a surface portion of the hydrous gel polymer is preferably crosslinked (surface-crosslinked) using a crosslinking agent in the drying process or any of subsequent processes. The surface crosslinking is preferably performed at a timing when the hydrous gel polymer has a specific water content. A timing of the surface crosslinking is preferably a time point at which a water content of the hydrous gel polymer is 5% to 50% by mass, is more preferably a time point at which a water content thereof is 10% to 40% by mass, and is even more preferably a time point at which a water content thereof is 15% to 35% by mass.

A water content (% by mass) of the hydrous gel polymer is calculated by the following formula.

Water content=$[Ww/(Ww+Ws)]\times100$

Ww: An amount of water of a hydrous gel polymer obtained by adding an amount of water used, as desired, upon mixing a powdery inorganic flocculating agent, a surface crosslinking agent, and the like to an amount obtained by subtracting an amount of water extracted to the outside of the system by the drying process from an amount of water contained in an aqueous liquid before polymerization in the all polymerization processes.

Ws: A solid fraction calculated from an amount of materials introduced, such as ethylenically unsaturated monomers, a crosslinking agent, and an initiator, each of which constitutes the hydrous gel polymer.

Examples of surface crosslinking agents for performing surface crosslinking include compounds having two or more reactive functional groups. Examples thereof include polyols such as ethylene glycol, propylene glycol, 1,4-butanediol, trimethylolpropane, glycerin, polyoxyethylene glycol, polyoxypropylene glycol, and polyglycerin; polyglycidyl compounds such as (poly)ethylene glycol diglycidyl ether, (poly)glycerin diglycidyl ether, (poly)glycerin triglycidyl ether, trimethylolpropane triglycidyl ether, (poly)propylene glycol polyglycidyl ether, and (poly)glycerol polyglycidyl ether; haloepoxy compounds such as epichlorohydrin, epibromohydrin, and α-methyl epichlorohydrin; isocyanate compounds such as 2,4-tolylene diisocyanate and hexamethylene diisocyanate; oxetane compounds such as 3-methyl-3-oxetane methanol, 3-ethyl-3-oxetane methanol, 3-butyl-3-oxetane methanol, 3-methyl-3-oxetane ethanol, 3-ethyl-3-oxetane ethanol, and 3-butyl-3-oxetane ethanol; oxazoline compounds such as 1,2-ethylenebisoxazoline; carbonate compounds such as ethylene carbonate; and hydroxyalkylamide compounds such as bis[N,N-di(β-hydroxyethyl)]adipamide. Among them, polyglycidyl compounds such as (poly)ethylene glycol diglycidyl ether, (poly)glycerin diglycidyl ether, (poly)glycerin triglycidyl ether, (poly)propylene glycol polyglycidyl ether, and polyglycerol polyglycidyl ether are more preferable. These surface crosslinking agents may be used alone or in combination of two or more kinds thereof.

In general, an amount of the surface crosslinking agent is preferably 0.00001 to 0.02 moles, is more preferably 0.00005 to 0.01 moles, and is even more preferably 0.0001 to 0.005 moles in a molar ratio, with respect to 1 mole of the ethylenically unsaturated monomer used in the polymerization, from the viewpoint of exhibiting suitable water absorption characteristics by appropriately crosslinking the obtained hydrous gel polymer.

A usage amount of the surface crosslinking agent is preferably 0.00001 moles or more from the viewpoint of sufficiently increasing a crosslinking density in a surface portion of the polymer particles and thereby enhancing gel strength of the water-absorbent resin particles. Furthermore, a usage amount thereof is preferably 0.02 moles or less from the viewpoint of increasing liquid suction power and increasing a water retention capacity of the water-absorbent resin particles.

It is possible to obtain polymer particles, which are a surface-crosslinked dried product, by distilling off water and the hydrocarbon dispersion medium by a known method after the surface crosslinking reaction.

A ratio of an amount of an external crosslinking agent to an amount of the internal crosslinking agent (hereinafter, also referred to as a "crosslinking proportion") of the polymer particles is preferably 10 or more, and is more preferably 12 or more, from the viewpoint of improving a value of non-pressurization DW after 3 minutes and liquid suction power. A crosslinking proportion may be, for example, 100 or less, 80 or less, 60 or less, 40 or less, 35 or less, 30 or less, or 25 or less. An amount of the internal crosslinking agent is a total amount (mmol) (used in production of polymer particles) of internal crosslinking agents added once or multiple times. An amount of the external crosslinking agent is a total amount (mmol) of an amount of a post-polymerization crosslinking agent and an amount of a surface crosslinking agent used in production of polymer particles.

The water-absorbent resin particles according to the present embodiment may be composed of only the polymer particles, but they can further contain, for example, various additional components selected from inorganic powders, surfactants, oxidizers, reducing agents, metal chelating agents (ethylenediaminetetraacetic acid and its salts, diethylenetriaminepentaacetic acid and its salts, for example, diethylenetriaminepentaacetic acid pentasodium, and the like), radical chain inhibitors, antioxidants, antibacterial agents, deodorants, gel stabilizers, flowability improvers (lubricants), and the like. The additional components may be disposed inside the polymer particles, on a surface of the polymer particles, or both of the inside and on the surface thereof.

The water-absorbent resin particles according to the present embodiment preferably contain inorganic particles. Examples of inorganic particles include silica particles such as amorphous silica. The amorphous silica may be hydrophilic amorphous silica. The inorganic particles can be disposed on the surface of the polymer particles by, for example, mixing the polymer particles and the inorganic particles. The inorganic particles referred to herein generally have a minute size as compared with a size of the polymer particles. For example, an average particle size of the inorganic particles may be 0.1 to 50 μm, 0.5 to 30 μm, or 1 to 20 μm. The average particle size referred to herein can be a value measured by a dynamic light scattering method or a laser diffraction/scattering method. In a case where an amount of the inorganic particles added is within the above range, it is easy to obtain water-absorbent resin particles having favorable water absorption characteristics.

For example, flowability of the water-absorbent resin particles can be improved by adding 0.05 to 5 parts by mass of amorphous silica as inorganic particles with respect to 100 parts by mass of the polymer particles. In a case where the water-absorbent resin particles contain inorganic particles, a ratio of the inorganic particles to a mass of the polymer particles may be 0.2% by mass or more, 0.5% by mass or more, 1.0% by mass or more, or 1.5% by mass or more, and it may be 5.0% by mass or less or 3.5% by mass or less.

A content of silica particles in the water-absorbent resin particles according to the present embodiment is preferably 1.8% by mass or less from the viewpoint of further inhibiting occurrence of tearing of the absorbent. A content of the silica particles may be 1.5% by mass or less, 1.0% by mass or less, 0.8% by mass or less, 0.5% by mass or less, or 0.3% by mass or less. A content of the silica particles in the water-absorbent resin particles according to the present embodiment may be, for example, 0.05% by mass or more or 0.1% by mass or more.

The water-absorbent resin particles according to the present embodiment have better absorbency for body fluids such as urine and blood, and they can be applied to, for example, the fields of sanitary products such as paper diapers, sanitary napkins, and tampons, and animal excrement treatment materials such as pet sheets, and dog or cat litters.

The water-absorbent resin particles according to the present embodiment can be suitably used for an absorbent. The absorbent according to the present embodiment includes the above-mentioned water-absorbent resin particles. A content of the water-absorbent resin particles in the absorbent is preferably 100 to 1,000 g per square meter (that is, 100 to 1,000 g/m$^2$), is more preferably 150 to 800 g/m$^2$, and is even more preferably 200 to 700 g/m$^2$ of the absorbent from the viewpoint that sufficient liquid absorption performances are then obtained when the absorbent is used for the absorbent article. A content thereof is preferably 100 g/m$^2$ or more from the viewpoint of exhibiting sufficient liquid absorption performances as the absorbent article, and thereby particularly inhibiting liquid leakage. A content thereof is preferably 1,000 g/m$^2$ or less from the viewpoint of inhibiting occurrence of a gel blocking phenomenon, and thereby exhibiting a diffusion performance of a liquid as the absorbent article and further improving a permeation speed of the liquid.

The absorbent may further include, for example, a fibrous material in addition to the water-absorbent resin particles. The absorbent may be, for example, a mixture containing the water-absorbent resin particles and the fibrous material. A mass proportion of the water-absorbent resin particles in the absorbent may be 2% by mass to 100% by mass, is preferably 10% by mass to 80% by mass, and is more preferably 20% by mass to 70% by mass, with respect to a total of the water-absorbent resin particles and the fibrous material. The configuration of the absorbent may be, for example, a form in which water-absorbent resin particles and the fibrous materials are uniformly mixed, a form in which water-absorbent resin particles are held between fibrous materials formed in a sheet shape or a layer shape, or another form.

Examples of fibrous materials include finely pulverized wood pulp; cotton; cotton linter; rayon; cellulose-based fibers such as cellulose acetate; and synthetic fibers such as polyamides, polyesters, and polyolefins. The fibrous material may be a mixture of the above-mentioned fibers.

Fibers may be adhered to each other by adding an adhesive binder to the fibrous material in order to enhance shape retention properties before or during use of the absorbent. Examples of adhesive binders include thermal bonding synthetic fibers, hot-melt adhesives, and adhesive emulsions. A usage amount of an adhesive binder can be reduced since the water-absorbent resin particles according to the present embodiment are better in shape retainability when used in an absorbent.

Examples of thermal bonding synthetic fibers include full-melt binders such as polyethylene, polypropylene, and an ethylene-propylene copolymer; and partial-melt binders formed of polypropylene and polyethylene in a side-by-side or core-and-sheath configuration. In the above-mentioned partial-melt binders, only a polyethylene portion is thermal-bonded. Examples of hot-melt adhesives include a blend of a base polymer such as an ethylene-vinyl acetate copolymer, a styrene-isoprene-styrene block copolymer, a styrene-butadiene-styrene block copolymer, a styrene-ethylene-butylene-styrene block copolymer, a styrene-ethylene-propylene-styrene block copolymer, and an amorphous polypropylene with a viscosity imparting agent, a plasticizer, an antioxidant, or the like.

Examples of adhesive emulsions include polymers of at least one or more monomers selected from the group consisting of methyl methacrylate, styrene, acrylonitrile, 2-ethylhexyl acrylate, butyl acrylate, butadiene, ethylene, and vinyl acetate. These adhesive binders may be used alone or in combination of two or more kinds thereof.

The absorbent according to the present embodiment may further contain additives such as inorganic powders (for example, amorphous silica), deodorants, pigments, dyes, antibacterial agents, fragrances, and pressure sensitive adhesives. These additives can impart various functions to the absorbent. In a case where the water-absorbent resin particles contain inorganic particles, the absorbent may contain an inorganic powder in addition to the inorganic particles in the water-absorbent resin particles. Examples of inorganic powders include silicon dioxide, zeolite, kaolin, clay, and the like.

A shape of the absorbent according to the present embodiment is not particularly limited, but it may be, for example, a sheet shape. A thickness of the absorbent (for example, a thickness of a sheet-shaped absorbent) may be, for example, 0.1 to 20 mm or 0.3 to 15 mm.

The absorbent article according to the present embodiment may include, for example, a core wrap, a liquid-permeable top sheet, and a liquid-impermeable back sheet, in addition to the absorbent. The core wrap retains the shape of the absorbent. The liquid-permeable top sheet is disposed on the outermost part on a side from which an absorption target liquid is infiltrated. The liquid-impermeable back sheet is disposed on the outermost part on a side opposite to the side from which the absorption target liquid is infiltrated.

Examples of the absorbent article include diapers (for example, paper diapers), toilet training pants, incontinence pads, sanitary products (sanitary napkins, tampons, and the like), sweat pads, pet sheets, portable toilet members, animal excrement treatment materials, and the like.

FIG. 1 is a cross-sectional view showing an example of an absorbent article. An absorbent article 100 shown in FIG. 1 includes an absorbent 10, core wraps 20a and 20b, a liquid-permeable top sheet 30, and a liquid-impermeable back sheet 40. In the absorbent article 100, the liquid-impermeable back sheet 40, the core wrap 20b, the absorbent 10, the core wrap 20a, and the liquid-permeable top sheet 30 are laminated in this order. In FIG. 1, there is a portion shown to be a gap between the members, but the members may be in close contact with each other without the gap.

The absorbent 10 has water-absorbent resin particles 10a and a fiber layer 10b containing a fibrous material. The water-absorbent resin particles 10a are dispersed in the fiber layer 10b.

The core wrap 20a is disposed on one surface side of the absorbent 10 (an upper side of the absorbent 10 in FIG. 1) in a state of being in contact with the absorbent 10. The core wrap 20b is disposed on the other surface side of the absorbent 10 (a lower side of the absorbent 10 in FIG. 1) in a state of being in contact with the absorbent 10. The absorbent 10 is disposed between the core wrap 20a and the core wrap 20b.

The core wrap 20a and the core wrap 20b each have, for example, a main surface having the same size as that of the absorbent 10. By using the core wraps, it is possible to maintain shape retainability of the absorbent and prevent the water-absorbent resin particles and the like constituting the absorbent from falling off and flowing. Examples of the core wraps include non-woven fabrics, woven fabrics, tissues, synthetic resin films having liquid permeation holes, net-like sheets having a mesh, and the like, of which tissues obtained by wet-type molding pulverized pulp are preferable from the viewpoint of economic efficiency.

The liquid-permeable top sheet 30 is disposed on the outermost part on a side from which an absorption target liquid is infiltrated. The liquid-permeable top sheet 30 is disposed on the core wrap 20a in a state of being in contact with the core wrap 20a. The liquid-impermeable back sheet 40 is disposed on the outermost part on a side opposite to the liquid-permeable top sheet 30, in the absorbent article 100. The liquid-impermeable back sheet 40 is disposed below the core wrap 20b in a state of being in contact with the core wrap 20b. The liquid-permeable top sheet 30 and the liquid-impermeable back sheet 40 each have, for example, a main surface wider than the main surface of the absorbent 10, and outer edges of the liquid-permeable top sheet 30 and the liquid-impermeable back sheet 40 respectively extend around the absorbent 10 and the core wraps 20a and 20b.

Examples of the liquid-permeable top sheet 30 include non-woven fabrics, porous sheets, and the like. Examples of non-woven fabrics include thermal bonded non-woven fabrics, air through non-woven fabrics, resin bonded non-woven fabrics, spunbond non-woven fabrics, melt-blown non-woven fabrics, spunbond/melt-blown/spunbond non-woven fabrics, airlaid non-woven fabrics, spunlace non-woven fabrics, point-bonded non-woven fabrics, and the like. Among them, thermal bonded non-woven fabrics, air through non-woven fabrics, spunbond non-woven fabrics, and spunbond/melt-blown/spunbond non-woven fabrics are preferably used.

As constituent materials for the liquid-permeable top sheet 30, it is possible to use resins or fibers known in the technical field. Examples thereof include polyolefins such as polyethylene (PE) and polypropylene (PP); polyesters such as polyethylene terephthalate (PET), polytrimethylene terephthalate (PTT), and polyethylene naphthalate (PEN); polyamides such as nylon; rayon; other synthetic resins or synthetic fibers; and fibers such as cotton, silk, hemp, and pulp (cellulose), from the viewpoint of liquid permeability, flexibility, and strength when the liquid-permeable top sheet 30 is used in an absorbent article. As the constituent material, synthetic fibers are preferably used from the viewpoint of increasing strength of the liquid-permeable top sheet 30. Among them, polyolefins and polyesters are preferable. These materials may be used alone or in combination of two or more materials.

It is desirable that a non-woven fabric used for the liquid-permeable top sheet 30 have appropriate hydrophilicity from the viewpoint of improving liquid absorption performances of the absorbent article. From this viewpoint, a non-woven fabric having a hydrophilicity of 5 to 200 is preferable, and a non-woven fabric having a hydrophilicity of 10 to 150 is more preferable, where the hydrophilicity is measured according to "Hydrophilicity of Non-woven fabric" (in accordance with Pulp and Paper Test Method No. 68 (2000)) disclosed in PCT International Publication No. WO2011/086843. Among the above-mentioned non-woven fabrics, a non-woven fabric having such a hydrophobicity may be formed of a material, such as rayon fibers, which shows an appropriate hydrophilicity by itself; or may be formed of fibers obtained by hydrophilizing hydrophobic chemical fibers such as polyolefin fibers and polyester fibers by a known method and imparting an appropriate hydrophilicity thereto.

Examples of methods of hydrophilizing chemical fibers include a method of obtaining a non-woven fabric by a spunbond technique from a mixture in which a hydrophilizing agent is added to hydrophobic chemical fibers in a spunbond non-woven fabric, a method of using a hydrophilizing agent when producing a spunbond non-woven fabric from hydrophobic chemical fibers, and a method of obtaining a spunbond non-woven fabric from hydrophobic chemical fibers, and thereafter impregnating the spunbond non-woven fabric with a hydrophilizing agent. As the hydrophilizing agent, the following examples are used: anionic surfactants such as aliphatic sulfonic acid salts and higher alcohol sulfuric acid ester salts; cationic surfactants such as quaternary ammonium salts; nonionic surfactants such as polyethylene glycol fatty acid esters, polyglycerin fatty acid esters, and sorbitan fatty acid esters; silicone surfactants such as polyoxyalkylene-modified silicone; stain release agents formed of polyester-based, polyamide-based, acrylic-based, or urethane-based resin; and the like.

It is preferable that a non-woven fabric used for the liquid-permeable top sheet 30 be moderately bulky and have a large weight per unit area from the viewpoint of imparting favorable liquid permeability, flexibility, strength, and cushioning properties to an absorbent article, and accelerating a liquid penetration speed of an absorbent article. A weight per unit area of the non-woven fabric is preferably 5 to 200 g/m$^2$, is more preferably 8 to 150 g/m$^2$, and is even more preferably 10 to 100 g/m$^2$. Furthermore, a thickness of the non-woven fabric is preferably 20 to 1,400 μm, is more preferably 50 to 1,200 μm, and is even more preferably 80 to 1,000 μm.

The liquid-impermeable back sheet 40 prevents a liquid absorbed by the absorbent 10 from leaking to the outside from the back sheet 40 side. For the liquid-impermeable back sheet 40, it is possible to use liquid-impermeable films mainly composed of polyolefin resins such as polyethylene (PE) and polypropylene (PP); breathable resin films; composite films in which a breathable resin film is bonded to a non-woven fabric such as spunbond non-woven fabric and spunlace non-woven fabric; spunbond/melt-blown/spunbond (SMS) non-woven fabrics in which a water-resistant melt blown non-woven fabric is sandwiched between high-strength spunbond non-woven fabrics; and the like. For the back sheet 40, it is possible to use a resin film having a weight per unit area of 10 to 50 g/m$^2$ and mainly made of low-density polyethylene (LDPE) resin from the viewpoint of ensuring flexibility so as not to impair a sensation of wearing the absorbent article. Furthermore, in a case where a breathable material is used, dampness generated when wearing the absorbent article is reduced, and thereby discomfort to a wearer can be reduced.

A magnitude relationship between the absorbent 10, the core wraps 20a and 20b, the liquid-permeable top sheet 30, and the liquid-impermeable back sheet 40 is not particularly limited, and it is appropriately adjusted according to usage applications and the like of the absorbent article. Furthermore, a method of retaining the shape of the absorbent 10 using the core wraps 20a and 20b is not particularly limited. The absorbent may be sandwiched by a plurality of the core wraps as shown in FIG. 1, or the absorbent may be covered with one core wrap.

The absorbent 10 may be adhered to the liquid-permeable top sheet 30. By adhering the absorbent 10 to the liquid-permeable top sheet 30, a liquid is more smoothly guided to the absorbent, and thereby it becomes easy to obtain an absorbent article that is further better in preventing liquid leakage. In a case where the absorbent 10 is sandwiched or covered by the core wrap, it is preferable that at least the core wrap and the liquid-permeable top sheet 30 be adhered to each other, and it is more preferable that the core wrap and the absorbent 10 be adhered to each other in addition to the adhesion of the core wrap and the liquid-permeable top sheet 30. Examples of methods of adhesion include a method of adhesion by applying a hot-melt adhesive to the liquid-permeable top sheet 30 in shapes such as a vertical stripe shape and a spiral shape at predetermined intervals in a width direction; a method of adhesion using a water-soluble binder selected from starch, carboxymethyl cellulose, polyvinyl alcohol, polyvinylpyrrolidone, and other water-soluble polymers; and the like. Furthermore, a method of adhesion by thermal bonding may be adopted in a case where the absorbent 10 contains thermal bonding synthetic fibers.

The present invention further provides a method for measuring liquid suction power. The method for measuring liquid suction power according to the present embodiment includes: causing water-absorbent resin particles to absorb a saturated amount of a test solution to obtain a swollen gel; placing water-absorbent resin particles (dried product), which are of the same type as the water-absorbent resin particles, on a gel layer formed from the swollen gel to obtain a test sample containing the gel layer and the water-absorbent resin particles; and measuring non-pressurization DW with the test sample as an evaluation target.

In the conventional non-pressurization DW measurement method, a suction performance is measured with water-absorbent resin particles (dried product) in a static state for a measurement target. That is, in the non-pressurization DW measurement method, a test solution is directly absorbed by a dried product of the water-absorbent resin particles. On the other hand, in the method for measuring liquid suction power according to the present embodiment, a test sample, which consists of a layer of a swollen gel (gel layer) that is swollen after a saturated amount of a solution is absorbed by the water-absorbent resin particles, and water-absorbent resin particles (dried product) dispersed on this gel layer, is used for an evaluation target. That is, in the method for measuring liquid suction power according to the present embodiment is different from the non-pressurization DW measurement method in that a layer of a swollen gel (gel layer) is present between a dried product of the water-absorbent resin particles and a test solution, where the layer is formed after a physiological saline solution is absorbed by water-absorbent resin particles of the same type. A value measured by the method for measuring liquid suction power according to the present embodiment is an amount (ml) of the test solution absorbed by the water-absorbent resin particles (dried product) dispersed on the gel layer of the test sample.

The test solution may be a solution generally used for measuring water absorption performances of the water-absorbent resin particles, and it may be, for example, a physiological saline solution (an aqueous solution of 0.9% by mass NaCl), ion exchange water, distilled water, artificial urine, or the like. A time for the test sample to absorb the test solution may be any time, and it can be, for example, 1 minute to 10 minutes.

An amount of suction of the test solution measured by the method for measuring liquid suction power according to the present embodiment is an amount of absorption of the test solution, that has passed through a swollen gel, by a dried product of the water-absorbent resin particles within a predetermined time, and it is thought that liquid permeability of the swollen gel affects the amount of suction. Accordingly, by measuring liquid suction power according to the present embodiment, it is possible to comprehensively measure the water absorption performances reflecting a suction ability of the water-absorbent resin particles and liquid permeability of the swollen gel obtained after water absorption. However, liquid suction power measured by the method for measuring liquid suction power according to the present embodiment does not necessarily correlate with Saline Flow Conductivity (SFC), which is a conventional evaluation of liquid permeability, or a value of the conventional non-pressurization DW described above, and this liquid suction power is suitable as a new item showing the properties of the water-absorbent resin particles.

The test sample in which a dried product of the water-absorbent resin particles is placed on a swollen gel is a test sample of quasi-reproduction of the state of the water-absorbent resin particles inside an absorbent when an absorbent article is used. Therefore, by using such a test sample, the water-absorbent resin particles can be evaluated in a state of conforming to a situation more similar to the actual situation.

The method for measuring liquid suction power can be used as a method for evaluating water absorption characteristics of the obtained water-absorbent resin particles when producing the water-absorbent resin particles. Accordingly, the present invention provides a method for producing water-absorbent resin particles, the method including evaluating liquid suction power of the water-absorbent resin particles by the above method for measuring liquid suction power. The above production method may include, for example, sorting out water-absorbent resin particles in which a value of liquid suction power after a predetermined time is equal to or more than a predetermined value.

EXAMPLES

Hereinafter, the present invention will be described in more detail with reference to examples, but the present invention is not limited to these examples.

<Production of Water-Absorbent Resin Particles>

[Example 1] A cylindrical round-bottomed separable flask was prepared, which had an inner diameter of 11 cm and a capacity of 2 L, and was equipped with a reflux condenser, a dropping funnel, a nitrogen gas introduction tube, and as a stirrer, a stirring blade having four inclined paddle blades, each having a blade diameter of 5 cm, in a two-tier manner. 293 g of n-heptane as a hydrocarbon dispersion medium was weighed into this flask, and 0.736 g of a maleic anhydride-modified ethylene-propylene copolymer (HI-WAX 1105A, Mitsui Chemicals, Inc.) as a polymeric dispersant was added thereinto. The reaction solution in the flask was heated to 80° C. while being stirred to dissolve the polymeric dispersant. Thereafter, the reaction solution was cooled to 50° C.

Meanwhile, 92.0 g (1.03 moles) of an aqueous solution of 80.5% by mass acrylic acid as an ethylenically unsaturated monomer was weighed into a beaker with an internal capacity of 300 ml, and 147.7 g of an aqueous solution of 20.9% by mass sodium hydroxide was added dropwise thereto while cooling the beaker from the outside to perform neutralization to 75 mol %. Thereafter, 0.092 g of hydroxyethyl cellulose (HEC AW-15F, manufactured by Sumitomo Seika Chemicals Co., Ltd.) as a thickener, 0.0736 g (0.272 mmol) of potassium persulfate as a radical polymerization agent, and 0.010 g (0.057 mmol) of ethylene glycol diglycidyl ether as an internal crosslinking agent were added and dissolved to prepare a first-stage aqueous liquid.

The prepared aqueous liquid was added into the reaction solution in the separable flask and stirred for 10 minutes. Then, a surfactant solution, in which 0.736 g of sucrose stearic acid ester (HLB: 3, Mitsubishi-Chemical Foods Corporation, RYOTO Sugar Ester S-370) as a surfactant was dissolved in 6.62 g of n-heptane by heating, was further added into the reaction solution. While stirring the reaction solution at 550 rpm as a rotational speed of the stirrer, the inside of the system was sufficiently replaced with nitrogen. Thereafter, the flask was immersed in a water bath at 70° C. to raise its temperature, and polymerization was performed for 60 minutes. Thereby, a first-stage polymerization slurry liquid was obtained.

Meanwhile, 128.8 g (1.43 moles) of an aqueous solution of 80.5% by mass acrylic acid as an ethylenically unsaturated monomer was weighed into another beaker with an internal capacity of 500 ml, and 159.0 g of an aqueous solution of 27% by mass sodium hydroxide was added dropwise thereto while cooling the beaker from the outside to perform neutralization to 75 mol %. Thereafter, as a radical polymerization initiator, 0.090 g (0.334 mmol) of potassium persulfate was added and dissolved to prepare a second-stage aqueous liquid.

While stirring at 1,000 rpm as a rotational speed of the stirrer, the inside of the separable flask system was cooled to 25° C. Then, a total amount of the second-stage aqueous liquid was added into the first-stage polymerization slurry liquid in the separable flask, and the inside of the system was replaced with nitrogen for 30 minutes. Thereafter, the flask was immersed in a water bath at 70° C. again to raise its temperature, and a polymerization reaction was performed for 60 minutes. Thereafter, 0.580 g (0.067 mmol) of an aqueous solution of 2% by mass ethylene glycol diglycidyl ether was added as a crosslinking agent for post-polymerization crosslinking, and thereby a hydrous gel polymer was obtained.

Under stirring, 0.265 g of an aqueous solution of 45% by mass diethylenetriaminepentaacetic acid pentasodium was added into the reaction solution containing the hydrous gel polymer obtained after the second-stage polymerization. Thereafter, the flask was immersed in an oil bath set to 125° C., and 253.9 g of water was extracted out of the system while n-heptane was refluxed by azeotropic distillation with n-heptane and water. Thereafter, 9.93 g (1.14 mmol) of an aqueous solution of 2% by mass ethylene glycol diglycidyl ether as a surface crosslinking agent was added into the flask, and maintained at 83° C. for 2 hours.

Thereafter, n-heptane was evaporated at 125° C., and the residue was dried to obtain polymer particles (dried product). These polymer particles were passed through a sieve having an aperture of 850 μm, and 0.5% by mass of amorphous silica (which is hydrophilic, Oriental Silicas Corporation, Tokusil NP-S) with respect to a mass of the polymer particles was mixed with the polymer particles. Thereby, 231.1 g of water-absorbent resin particles containing the amorphous silica was obtained. A median particle size of the water-absorbent resin particles was 357 μm. A ratio of the amount of the external crosslinking agent to the amount of the internal crosslinking agent (crosslinking proportion) was 21.1. An amount of the internal crosslinking agent is a total amount (mmol) of internal crosslinking agents added once or twice. An amount of the external crosslinking agent is a total amount (mmol) of an amount of a post-polymerization crosslinking agent and an amount of a surface crosslinking agent.

[Example 2] 230.8 g of water-absorbent resin particles was obtained in the same manner as in Example 1 except that an amount of water extracted out of the system by azeotropic distillation was changed to 259.4 g, an amount of an aqueous solution of ethylene glycol diglycidyl ether as a surface crosslinking agent was changed to 6.30 g (0.723 mmol), and a blending amount of amorphous silica with respect to polymer particles (dried product) was changed to 0.1% by mass. A median particle size of the water-absorbent resin particles was 349 sun. A crosslinking proportion was 13.9.

[Example 3] 229.6 g of water-absorbent resin particles was obtained in the same manner as in Example 1 except that, in preparation of a first-stage aqueous liquid, 0.092 g (0.339 mmol) of 2,2'-azobis(2-amidinopropane) dihydrochloride was added as a radical polymerization agent, an amount of potassium persulfate as a radical polymerization agent was changed to 0.018 g (0.068 mmol), and an amount of ethylene glycol diglycidyl ether as an internal crosslinking agent was changed to 0.0045 g (0.026 mmol); in preparation of a second-stage aqueous liquid, 0.129 g (0.475 mmol) of 2,2'-azobis(2-amidinopropane) dihydrochloride was added as a radical polymerization agent, and an amount of potassium persulfate as a radical polymerization agent was changed to 0.026 g (0.095 mmol); an amount of water extracted out of the system by azeotropic distillation was changed to 241.6 g; an amount of an aqueous solution of ethylene glycol diglycidyl ether as a surface crosslinking agent was changed to 6.40 g (0.735 mmol); and a blending amount of amorphous silica with respect to polymer particles (dried product) was changed to 0.2% by mass. A median particle size of the water-absorbent resin particles was 342 μm. A crosslinking proportion was 30.8.

[Example 4] 231.1 g of water-absorbent resin particles was obtained in the same manner as in Example 3 except that an amount of water extracted out of the system by azeotropic distillation was changed to 248.2 g. A median particle size of the water-absorbent resin particles was 355 μm. A crosslinking proportion was 30.8.

[Comparative Example 1] 230.8 g of water-absorbent resin particles was obtained in the same manner as in Example 2 except that a blending amount of amorphous silica with respect to polymer particles (dried product) was changed to 0.5% by mass. A median particle size of the water-absorbent resin particles was 349 μm. A crosslinking proportion was 13.9.

[Comparative Example 2] 230.8 g of water-absorbent resin particles was obtained in the same manner as in Comparative Example 1 except that a blending amount of amorphous silica with respect to polymer particles (dried product) was changed to 2.0% by mass. A median particle size of the water-absorbent resin particles was 349 n. A crosslinking proportion was 13.9.

[Comparative Example 3] 231.0 g of water-absorbent resin particles was obtained in the same manner as in Example 1 except that, in preparation of a second-stage aqueous liquid, 0.0117 g (0.067 mmol) of ethylene glycol diglycidyl ether was added as an internal crosslinking agent; a crosslinking agent for post-polymerization crosslinking was not added; an amount of water extracted out of the system by azeotropic distillation was changed to 269.2 g; an amount of an aqueous solution of ethylene glycol diglycidyl ether as a surface crosslinking agent was changed to 1.98 g (0.228 mmol); and a blending amount of amorphous silica with respect to polymer particles (dried product) was changed to 0.1% by mass. A median particle size of the water-absorbent resin particles was 347 μm. A crosslinking proportion was 1.8.

[Comparative Example 4] 230.6 g of water-absorbent resin particles was obtained in the same manner as in Comparative Example 3 except that an amount of water extracted out of the system by azeotropic distillation was changed to 271.4 g, an amount of an aqueous solution of ethylene glycol diglycidyl ether as a surface crosslinking agent was changed to 6.40 g (0.735 mmol), and a blending amount of amorphous silica with respect to polymer particles (dried product) was changed to 0.5% by mass. A median particle size of the water-absorbent resin particles was 355 μm. A crosslinking proportion was 5.9.

[Comparative Example 5] 231.1 g of water-absorbent resin particles was obtained in the same manner as in Example 1 except that a blending amount of amorphous silica with respect to polymer particles (dried product) was changed to 2.0% by mass. A median particle size of the water-absorbent resin particles was 357 μm. A crosslinking proportion was 21.2.

[Comparative Example 6] 230.3 g of water-absorbent resin particles was obtained in the same manner as in Example 1 except that, in preparation of a first-stage aqueous liquid, an amount of ethylene glycol diglycidyl ether as an internal crosslinking agent was changed to 0.011 g (0.063 mmol); in preparation of a second-stage aqueous liquid, 0.013 g (0.075 mmol) of ethylene glycol diglycidyl ether was added as an internal crosslinking agent; a crosslinking agent for post-polymerization crosslinking was not added; an amount of water extracted out of the system by azeotropic distillation was changed to 275.6 g; and amorphous silica with respect to polymer particles was not added. A median particle size of the water-absorbent resin particles was 349 μm. A crosslinking proportion was 8.3.

The obtained water-absorbent resin particles were evaluated for a water retention capacity for a physiological saline solution, a median particle size, a value of non-pressurization DW after 3 minutes, a value of liquid suction power after 3 minutes, and absorbent tearing properties by the following method. The physiological saline solution used in the present example was an aqueous solution of 0.9% by mass NaCl.

<Measurement of water retention capacity for physiological saline solution> A cotton bag (cotton broadcloth No. 60, 100 mm in width×200 mm in length) into which 2.0 g of the water-absorbent resin particles had been weighed was placed in a beaker having a capacity of 500 ml. 500 g of a physiological saline solution was poured into the cotton bag containing the water-absorbent resin particles at once so that a lump could not be produced. The upper part of the cotton bag was bound with a rubber band and left to stand for 30 minutes, and thereby the water-absorbent resin particles were swollen. The cotton bag after an elapse of 30 minutes was dehydrated for 1 minute using a dehydrator (manufactured by KOKUSAN Co., Ltd., product number: H-122) which had been set at a centrifugal force of 167 G, and a mass Wa (g) of the dehydrated cotton bag containing the swollen gel was measured. By performing the same operation without addition of the water-absorbent resin particles, a mass Wb (g) of an empty cotton bag upon moisturizing was measured, and a water retention capacity for a physiological saline solution was calculated by the following formula. The results are shown in Table 1.

Water retention capacity for physiological saline solution $(g/g) = [Wa - Wb]/2.0$ <Measurement of median particle size (particle size distribution)> 50 g of the water-absorbent resin particles was used for measuring a median particle size (particle size distribution). JIS standard sieves were combined in the following order from the top: a sieve having an aperture of 850 μm, a sieve having an aperture of 500 μm, a sieve having an aperture of 425 μm, a sieve having an aperture of 300 μm, a sieve having an aperture of 250 μm, a sieve having an aperture of 180 μm, a sieve having an aperture of 150 μm, and a receiving tray.

The water-absorbent resin particles were fed to the topmost sieve among the combination of the sieves, shaken for 20 minutes using a Ro-Tap shaker, and thereby classified. After the classification, a mass of the water-absorbent resin particles remaining on each of the sieves was calculated as a mass percentage with respect to a total amount to determine a particle size distribution. By integrating values on the sieves in descending order of the particle sizes with regard to the particle size distribution, a relationship between the aperture of the sieve and the integrated value of mass percentages of the water-absorbent resin particles remaining on the sieve was plotted on a log-probability paper. The plotted points on the probability paper were connected with straight lines, and a particle size corresponding to 50% by mass of the integrated mass percentage was taken as a median particle size.

Figure 2:
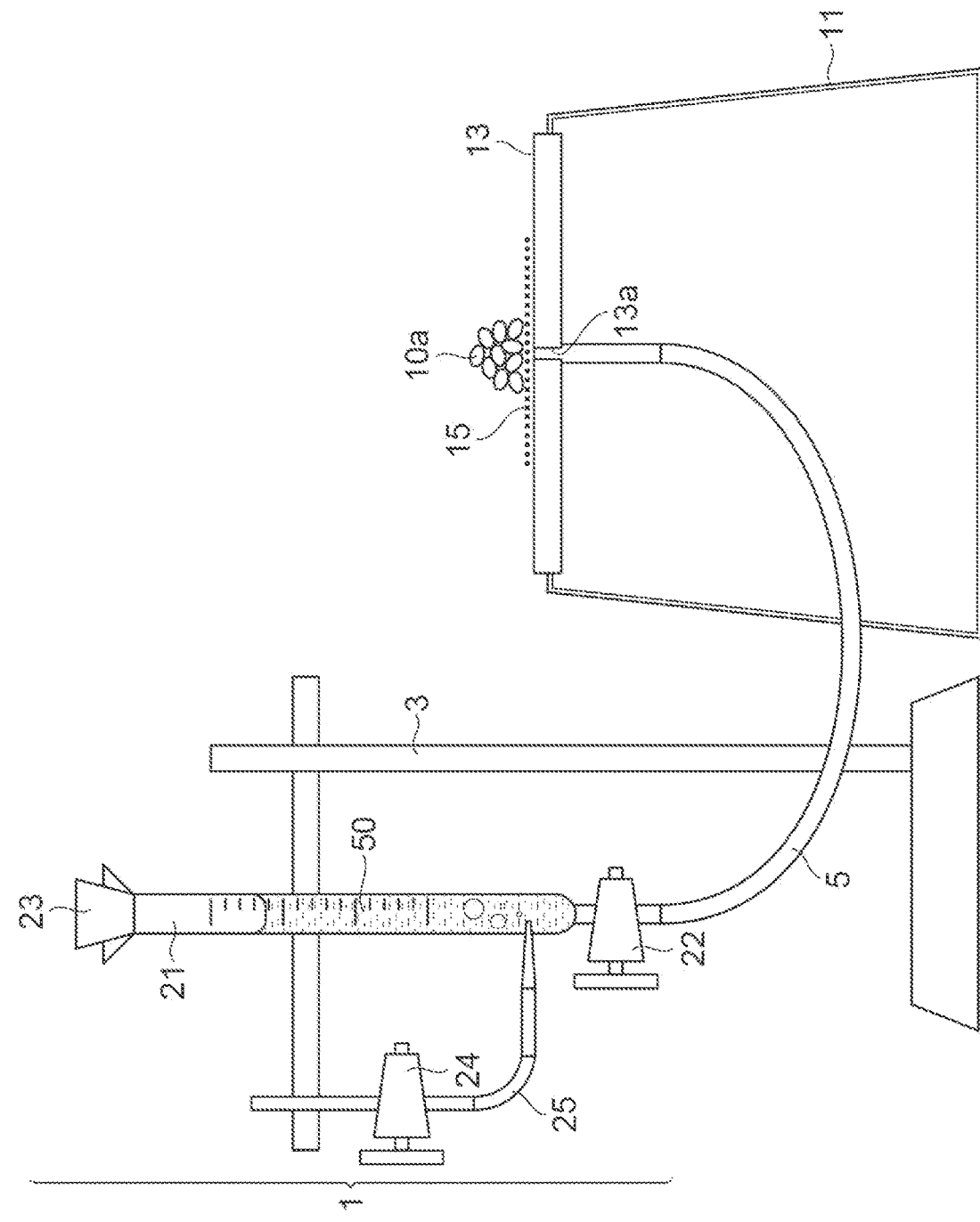
FIG. 2 is a schematic view showing a method for measuring non-pressurization DW.

<Measurement of non-pressurization DW> Non-pressurization DW of the water-absorbent resin particles was measured using a measuring device shown in FIG. 2. The measurement was carried out five times for one type of water-absorbent resin particles, and an average value of three measurement values excluding a minimum value and a maximum value was obtained.

The measuring device has a burette part 1, a conduit pipe 5, a measuring stand 13, a nylon mesh sheet 15, a stand 11, and a clamp 3. The burette part 1 has a burette tube 21 on which a scale is engraved, a rubber stopper 23 for sealing an opening at an upper part of the burette tube 21, a cock 22 connected to a tip end of a lower part of the burette tube 21, an air introducing pipe 25 connected to the lower part of the burette tube 21, and a cock 24. The burette part 1 is fixed by the clamp 3. The flat plate-shaped measuring stand 13 has a through-hole 13a having a diameter of 2 mm and formed in the center portion of the measuring stand 13, and is supported by the height-variable stand 11. The through-hole 13a of the measuring stand 13, and the cock 22 of the burette part 1 are connected by the conduit pipe 5. An inner diameter of the conduit pipe 5 is 6 mm.

The measurement was performed in the environment of a temperature of 25° C. and a humidity of 60±10%. First, the cock 22 and the cock 24 of the burette part 1 were closed, and a physiological saline solution 50 that had been adjusted to 25° C. was put into the burette tube 21 through the opening at the upper part of the burette tube 21. A concentration (0.9% by mass) of the physiological saline solution is a concentration based on a mass of an aqueous solution of NaCl. The opening of the burette tube 21 was sealed with the rubber stopper 23, and then the cock 22 and the cock 24 were opened. The inside of the conduit pipe 5 was filled with the 0.9% by mass saline solution 50 to prevent air bubbles from entering. A height of the measuring stand 13 was adjusted so that a height of a water surface of the physiological saline solution, which had reached the inside of the through-hole 13a, was the same as a height of an upper surface of the measuring stand 13. After the adjustment, the height of the water surface of the physiological saline solution 50 in the burette tube 21 was read by the scale on the burette tube 21, and this position was defined as a zero point (value read at 0 seconds).

The nylon mesh sheet 15 (100 mm×100 mm, 250 mesh, thickness about 50 μm) was laid in the vicinity of the through-hole 13a on the measuring stand 13, and a cylinder having an inner diameter of 30 mm and a height of 20 mm was placed on the center portion of the nylon mesh sheet. 1.00 g of water-absorbent resin particles 10a were uniformly dispersed in this cylinder. Thereafter, the cylinder was carefully removed to obtain a sample in which the water-absorbent resin particles 10a were dispersed in a circle shape in the center portion of the nylon mesh sheet 15. Then, the nylon mesh sheet 15 on which the water-absorbent resin particles 10a were placed was moved at a high speed to the extent that the water-absorbent resin particles 10a did not dissipate so that the center of the nylon mesh sheet was at the position of the through-hole 13a, and the measurement was started. A timing when air bubbles were first introduced from the air introducing pipe 25 into the burette tube 21 was defined as a start of water absorption (0 seconds).

An amount of decrease in the physiological saline solution 50 in the burette tube 21 (that is, an amount of the physiological saline solution absorbed by the water-absorbent resin particles 10a) was sequentially read by units of 0.1 ml, and a reduction in weight Wc (g) of the physiological saline solution 50 was read 3 minutes after the start of water absorption by the water-absorbent resin particles 10a. A value of non-pressurization DW after 3 minutes was obtained from Wc by the following formula. The non-pressurization DW is a water absorption capacity per 1.00 g of the water-absorbent resin particles 10a. The results are shown in Table 1.

Value of non-pressurization $DW$ after 3 minutes (ml/g)=$Wc/1.00$

<Measurement of Liquid Suction Power>

Figure 3:
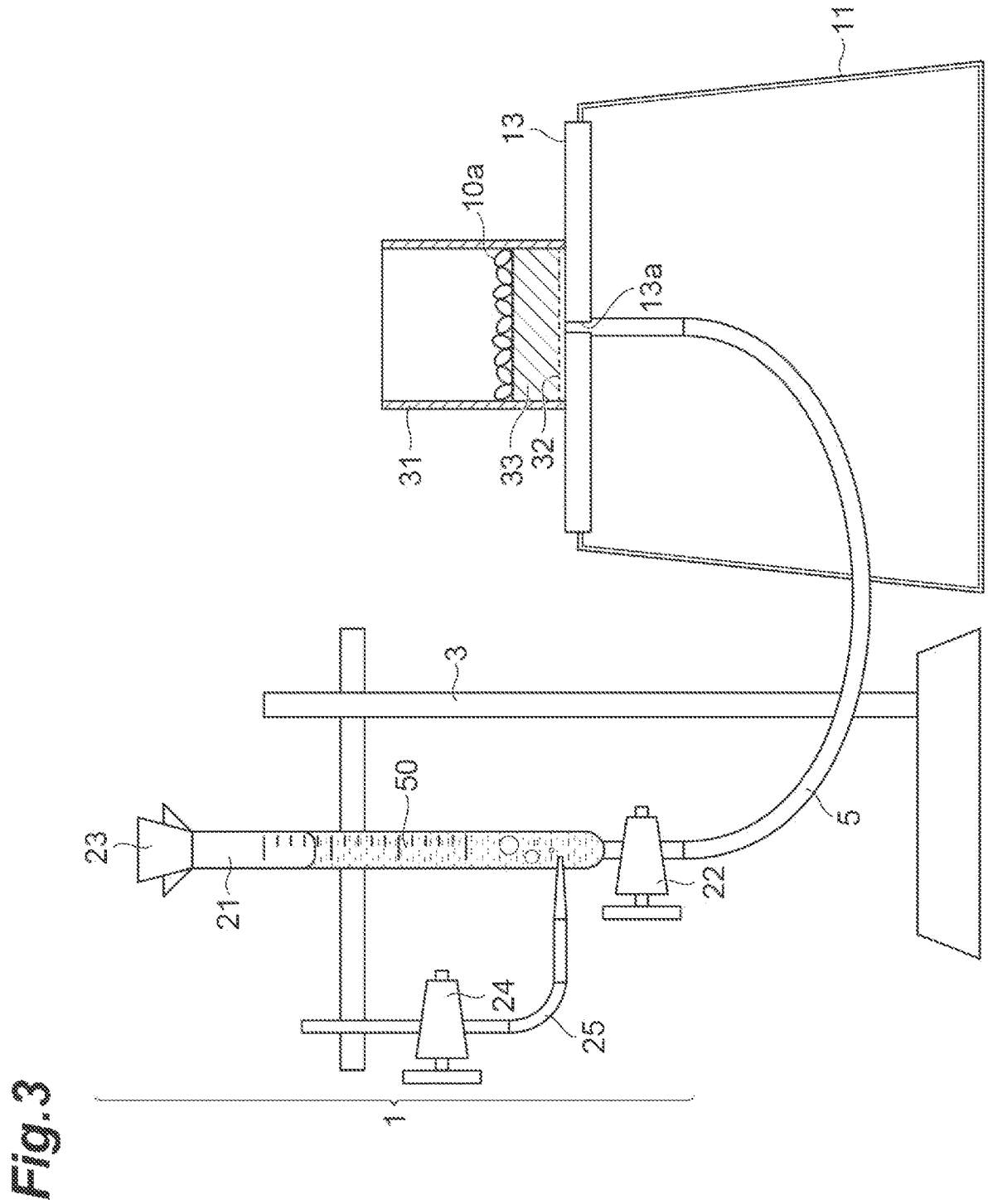
FIG. 3 is a schematic view showing an example of a method for measuring liquid suction power.

[Measuring device] Liquid suction power of the water-absorbent resin particles was measured using a measuring device shown in FIG. 3. The measurement was carried out five times for one type of water-absorbent resin particles, and an average value of three measurement values excluding a minimum value and a maximum value was obtained.

The measuring device has a burette part 1, a conduit pipe 5, a measuring stand 13, a nylon mesh sheet 15, a stand 11, and a clamp 3. Details thereof are the same as those in the non-pressurization DW measurement values shown in FIG. 2.

The measurement was performed in the environment of a temperature of 25° C. and a humidity of 60±10%. First, the cock 22 and the cock 24 of the burette part 1 were closed, and a physiological saline solution 50 that had been adjusted to 25° C. was put into the burette tube 21 through the opening at the upper part of the burette tube 21. A concentration of the physiological saline solution (0.9% by mass) is a concentration based on a mass of an aqueous solution of NaCl. The opening of the burette tube 21 was sealed with the rubber stopper 23, and then the cock 22 and the cock 24 were opened. The inside of the conduit pipe 5 was filled with the physiological saline solution 50 to prevent air bubbles from entering. A height of the measuring stand 13 was adjusted so that a height of a water surface of the physiological saline solution, which had reached the inside of the through-hole 13a, was the same as a height of an upper surface of the measuring stand 13. After the adjustment, the height of the water surface of the physiological saline solution 50 in the burette tube 21 was read by the scale on the burette tube 21, and this position was defined as a zero point (value read at 0 seconds).

[Preparation of sample] 0.3 g of water-absorbent resin particles was uniformly put into a cylindrical container 31, which was made of acrylic resin, which had an inner diameter of 26 mm, an outer diameter of 40 mm, and a height of 140 mm, and in which a nylon mesh sheet 32 (250 mesh) was adhered to a lower end opening thereof. A wire mesh (aperture 10 mesh) having a height of 2 mm and a size of 50×50 mm was placed in a petri dish having an inner diameter of about 70 mm, and 40 g of a physiological saline solution was added thereinto. The cylindrical container containing the water-absorbent resin particles was placed on the wire mesh, the water-absorbent resin particles were caused to absorb the physiological saline solution for 30 minutes, and thereby a swollen gel 33 was obtained. The cylindrical container 31 containing the swollen gel 33 was taken out from the petri dish, and another 0.3 g of water-absorbent resin particles 10a (dried product) was uniformly dispersed on the swollen gel 33 in the cylindrical container 31.

[Measurement of liquid suction power] Immediately after dispersing the resin particles, the cylindrical container 31 containing the swollen gel 33 and the water-absorbent resin particles 10*a* was placed on the measuring stand 13 so that the center of the cylindrical container 31 was positioned on the through-hole 13*a*, and the measurement was started. A timing when air bubbles were first introduced from the air introducing pipe 25 into the burette tube 21 was defined as a start of water absorption (0 seconds).

An amount of decrease in the physiological saline solution 50 in the burette tube 21 was sequentially read by units of 0.1 ml, and a reduction in weight Wd (g) of the physiological saline solution 50 was read 3 minutes after the start of water absorption by the water-absorbent resin particles 10*a*. A value of liquid suction power after 3 minutes was obtained from Wd by the following formula. The liquid suction power is a water absorption capacity per 1.00 g of the water-absorbent resin particles 10*a*. The results are shown in Table 1.

Value of liquid suction power after 3 minutes
(ml/g)=Wd/0.3

<Measurement of Absorbent Tearing Properties>

[Production of absorbent article for evaluation] 10 g of the water-absorbent resin particles and 6.67 g of pulverized pulp were uniformly mixed by air papermaking using a Padformer manufactured by O-tec Co., Ltd., and thereby an absorbent having a size of 40 cm×12 cm was produced. 0.4 g of ion exchange water was sprayed with a spray on the absorbent placed on a tissue paper having a size of 42 cm×14 cm and a weight per unit area of 16 g/m$^2$, another tissue of 40 cm 12 cm was placed on this absorbent, and thereby a laminate was produced. Next, a wire mesh having a size of 62 cm×22 cm and having an aperture of 2 mm was placed on the laminate, and the laminate was pressed at a pressure of 0.141 MPa using a press machine (small-sized air type press machine, Imoto Machinery Co., Ltd.). After the pressing, the wire mesh was removed from the laminate.

Portions at a distance of 15 cm away in a longitudinal direction from the center portion of the pressed laminate were each cut with a roll cutter so that a length of became 30 cm. The laminate was sandwiched between two polyethylene air-through type porous liquid-permeable sheets (hereinafter, also referred to as "liquid-permeable sheets") having a weight per unit area of 22 g/m$^2$ and a size of 34 cm×14 cm. Four sides of the two liquid-permeable sheets sandwiching the laminate were crimped by a heat sealer (Fuji Impulse Sealer, model number: FI-450-5 type, manufactured by FUJI IMPULSE CO., LTD.), and thereby an absorbent article for evaluation was obtained. At the time of crimping, a portion of the tissue protruded from the absorbent was crimped by sandwiching the protruding tissue with the liquid-permeable sheets.

[Preparation of test solution] An appropriate amount of distilled water was put into a 10 L container, and 100 g of sodium chloride, 3.0 g of a calcium chloride dihydrate, and 6.0 g of a magnesium chloride hexahydrate were added and dissolved therein. Then, 0.25 g of polyoxyethylene nonylphenyl ether was added thereto, and distilled water was further added so that a total mass became 10 kg. Furthermore, the mixed solution was colored with a small amount of Blue No. 1, and thereby a test solution for measuring tearing properties was prepared.

Figure 4:
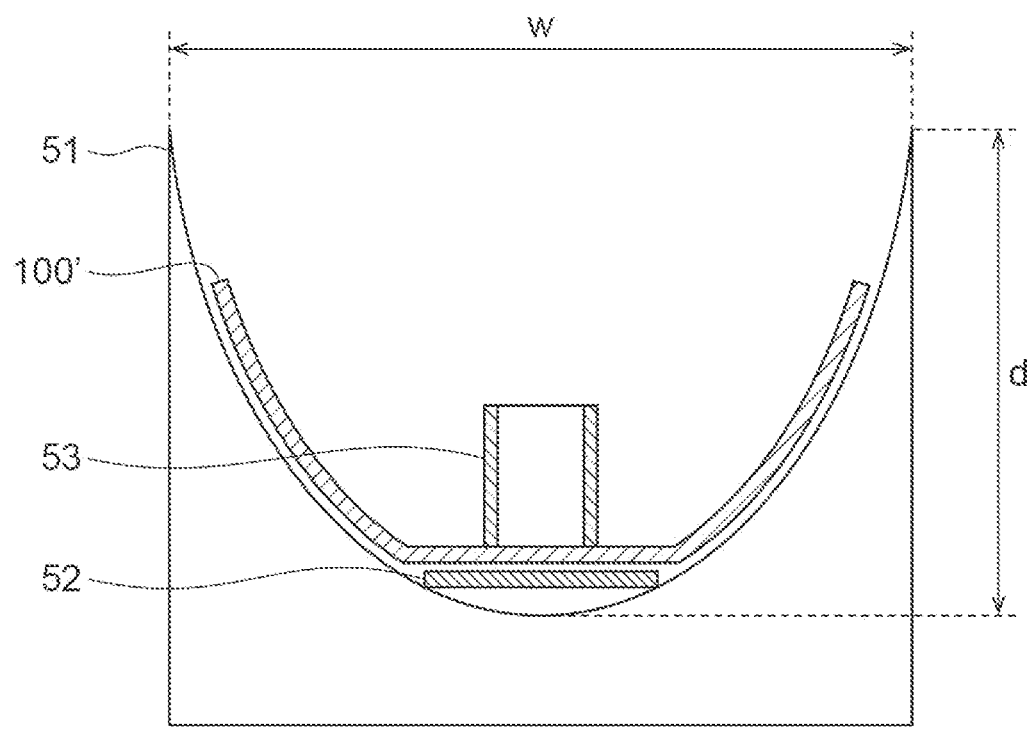
FIG. 4 is a schematic view showing a method for measuring an absorbent tearing time.

[Measurement of absorbent tearing time] An absorbent tearing time was measured in a room at a temperature of 25° C.±2° C. using a U-shaped instrument 51 (depth 14 cm, made of acryl) shown in FIG. 4. In the U-shaped instrument 51, an opening width w was 21 cm, and a depth d was 18.5 cm. The U-shaped instrument 51 was used so that the opening was upward. A paperboard 52 with 14 cm×6.5 cm was placed on a U-shaped bottom portion to form a flat bottom portion with width 6.5 cm×depth 14 cm. An absorbent article 100' for evaluation was placed on the U-shaped instrument 51 so that the center of the absorbent article 100' for evaluation was matched with the center of the paperboard 52. A cylindrical cylinder 53 having an inner diameter of 2 cm, an outer diameter of 3 cm, a height of 6.5 cm, and a weight of 60 g was put on the center of the absorbent article 100' for evaluation, and 80 ml of the above test solution adjusted to 25° C.±1° C. was added into the cylinder 53. During the addition of the test solution, the addition was continued to maintain a height of a liquid level of the test solution at about 5 cm from the bottom of the cylinder.

After the entire test solution added into the cylinder 53 was absorbed by the absorbent article 100' for evaluation, the cylinder 53 on the absorbent article 100' for evaluation was removed. The cylinder 53 was put on the center of the absorbent article 100' for evaluation again 3 minutes after start of adding the test solution, and 80 ml of the test solution was added and absorbed by the absorbent article 100' for evaluation in the same manner as described above.

The absorbent article 100' for evaluation was placed on a paperboard (weight per unit area 3,500 g/m$^2$) having the same size as that of the absorbent article 100' for evaluation 6 minutes after start of the first addition of the test solution. Both ends in a longitudinal direction were bonded with an adhesive tape to fix the absorbent article 100' for evaluation to the paperboard. The fixed absorbent article 100' for evaluation was put into a transparent polyethylene bag (40 cm×28 cm, thickness 0.04 mm, Unipack, manufactured by SEISANNIPPONSHA LTD., K-4) which was attached with a zipper and in which a 1-cm cut was made at three points to remove air after sealing. The absorbent article 100' for evaluation was put into the transparent bag so that the corner of the bag and the corner of the absorbent article 100' for evaluation were matched with each other, the remaining part of the bag was folded back and fixed with an adhesive tape, and the entire bag became approximately the same size as the absorbent article 100' for evaluation.

The packed absorbent article 100' for evaluation was centrifuged 11 minutes after start of the first addition of the test solution at a centrifugal force of 27.5 G (rotational speed: 405 r/min). The centrifugation was performed in a state in which the packed absorbent article 100' for evaluation was fixed with a packing tape on a turntable with a diameter of 30 cm so that the surface of the absorbent article 100' for evaluation was perpendicular to a rotation shaft, and the rotation shaft was at the center of the absorbent article 100' for evaluation.

The centrifugation was interrupted every 1 minute from the start of centrifugation until 4 minutes, and every 2 minutes after 4 minutes from the start of centrifugation, and the presence or absence of tearing of the absorbent after liquid absorption was visually confirmed. A total centrifugation time until tearing was recognized was defined as a tearing time. In a case where the measurement was carried out for up to 20 minutes but tearing of the absorbent was not recognized, it was evaluated as "20 minutes or longer." The results are shown in Table 1.

TABLE 1

| | Water retention capacity [g] | Value of non-pressurization DW after 3 minutes [ml/g] | Value of liquid suction power after 3 minutes [ml/g] | Absorbent tearing time [min] |
| --- | --- | --- | --- | --- |
| Example 1 | 35 | 32 | 15.7 | 20 or longer |
| Example 2 | 41 | 27 | 13.7 | 20 or longer |
| Example 3 | 44 | 15 | 22.7 | 20 or longer |
| Example 4 | 51 | 20 | 17.3 | 20 or longer |
| Comparative Example 1 | 41 | 49 | 10.0 | 6 |
| Comparative Example 2 | 41 | 49 | 4.0 | 1 |
| Comparative Example 3 | 50 | 19 | 3.3 | 1 |
| Comparative Example 4 | 45 | 54 | 5.3 | 4 |
| Comparative Example 5 | 35 | 49 | 10.2 | 8 |
| Comparative Example 6 | 40 | 12 | 19.3 | 10 |

It was confirmed that the absorbents, which were formed using the water-absorbent resin particles obtained in the examples in which a value of non-pressurization DW after 3 minutes and a value of liquid suction power after 3 minutes were each equal to or higher than certain values, had a tearing time of 20 minutes or longer, and occurrence of tearing of the absorbent after liquid absorption was inhibited. On the other hand, it was confirmed that tearing after liquid absorption occurred at an earlier stage in the absorbents formed using the water-absorbent resin particles obtained in the comparative examples.

REFERENCE SIGNS LIST

1 burette part, 3 clamp, 5 conduit pipe, 10 absorbent, 10a water-absorbent resin particle, 10b fiber layer, 11 stand, 13 measuring stand, 13a through-hole, 15 nylon mesh sheet, 20a, 20b core wrap, 21 burette tube, 22 cock, 23 rubber stopper, 24 cock, air introducing pipe, 30 liquid-permeable top sheet, 31 cylindrical container, 32 nylon mesh sheet, 33 swollen gel, 40 liquid-impermeable back sheet, 50 physiological saline solution, 51 U-shaped instrument, 52 paperboard, 53 cylindrical cylinder, 100, 100' absorbent article

The invention claimed is:

1. Water-absorbent resin particles,
wherein a value of non-pressurization DW after 3 minutes is 14 ml/g or more and 40 ml/g or less, and a value of liquid suction power after 3 minutes measured by the following method is 11 ml/g or more and 25 ml/g or less,
wherein the water-absorbent resin particles comprise a crosslinked polymer having a structural unit derived from (meth)acrylic acid and a salt thereof,
wherein a content of silica particles in the water-absorbent resin particles is 0.05 mass % or more based on the total amount of the water-absorbent resin particles, and
wherein a water retention capacity for a physiological saline solution is 37 g/g or more,
a liquid suction power measurement method: 0.3 g of the water-absorbent resin particles is uniformly dispersed in a cylindrical container having a mesh-like bottom and having an inner diameter of 26 mm; the cylindrical container is placed in a container containing 40 g of a physiological saline solution, the water-absorbent resin particles are caused to absorb the physiological saline solution for 30 minutes from the bottom of the cylindrical container, and thereby a swollen gel is obtained; and non-pressurization DW, which is measured in a state where another 0.3 g of the water-absorbent resin particles is uniformly dispersed on the swollen gel in the cylindrical container, is defined as liquid suction power.

2. The water-absorbent resin particles according to claim 1, wherein a content of silica particles is 1.8% by mass or less.

3. An absorbent comprising the water-absorbent resin particles according to claim 1.

4. An absorbent article comprising the absorbent according to claim 3.

5. The absorbent article according to claim 4, wherein the article is a diaper.

* * * * *